United States Patent [19]
Kagaya

[11] Patent Number: 5,463,668
[45] Date of Patent: Oct. 31, 1995

[54] X-RAY DIAGNOSIS APPARATUS

[75] Inventor: Shinichiro Kagaya, Tochigi, Japan

[73] Assignee: Kabushiki Kaisha Toshiba, Kawasaki, Japan

[21] Appl. No.: 305,894

[22] Filed: Sep. 14, 1994

[30] Foreign Application Priority Data

| Sep. 14, 1993 | [JP] | Japan | 5-229013 |
| Apr. 8, 1994 | [JP] | Japan | 6-070555 |
| Sep. 6, 1994 | [JP] | Japan | 6-212454 |

[51] Int. Cl.$^6$ .................................................. A61B 6/00
[52] U.S. Cl. .................... 378/98.2; 378/98.3; 378/98.12; 378/196
[58] Field of Search ................. 378/98.2, 98.3, 378/98.7, 98.8, 98.12, 62, 145, 146, 193, 195, 196, 197, 198, 205

[56] References Cited

U.S. PATENT DOCUMENTS

| 4,411,012 | 10/1983 | Pfeifer et al. | 378/146 X |
| 5,090,037 | 2/1992 | Toth et al. | 378/146 X |
| 5,293,574 | 3/1994 | Roehm et al. | 378/98.2 |
| 5,347,570 | 9/1994 | Haaks | 378/98.12 |

FOREIGN PATENT DOCUMENTS 1-211900  8/1989  Japan.

*Primary Examiner*—David P. Porta
*Attorney, Agent, or Firm*—Oblon, Spivak, McClelland, Maier & Neustadt

[57] ABSTRACT

An X-ray diagnosis apparatus comprises a bed on which an object is placed, supporter on which X-ray irradiation unit for irradiating a predetermined amount of X-rays to the object on the bed and converting unit for converting X-rays passed through the object into an object image signal are mounted, first moving unit for moving the bed, second moving unit for moving the supporter, and drive control unit for controlling movement of at least the converting unit in such a manner that the object appears to be stopped as viewed from the converting unit while the bed and the supporter are moved relative to each other by the first moving unit and the second moving unit and X-rays are irradiated from the X-ray irradiation unit.

24 Claims, 15 Drawing Sheets

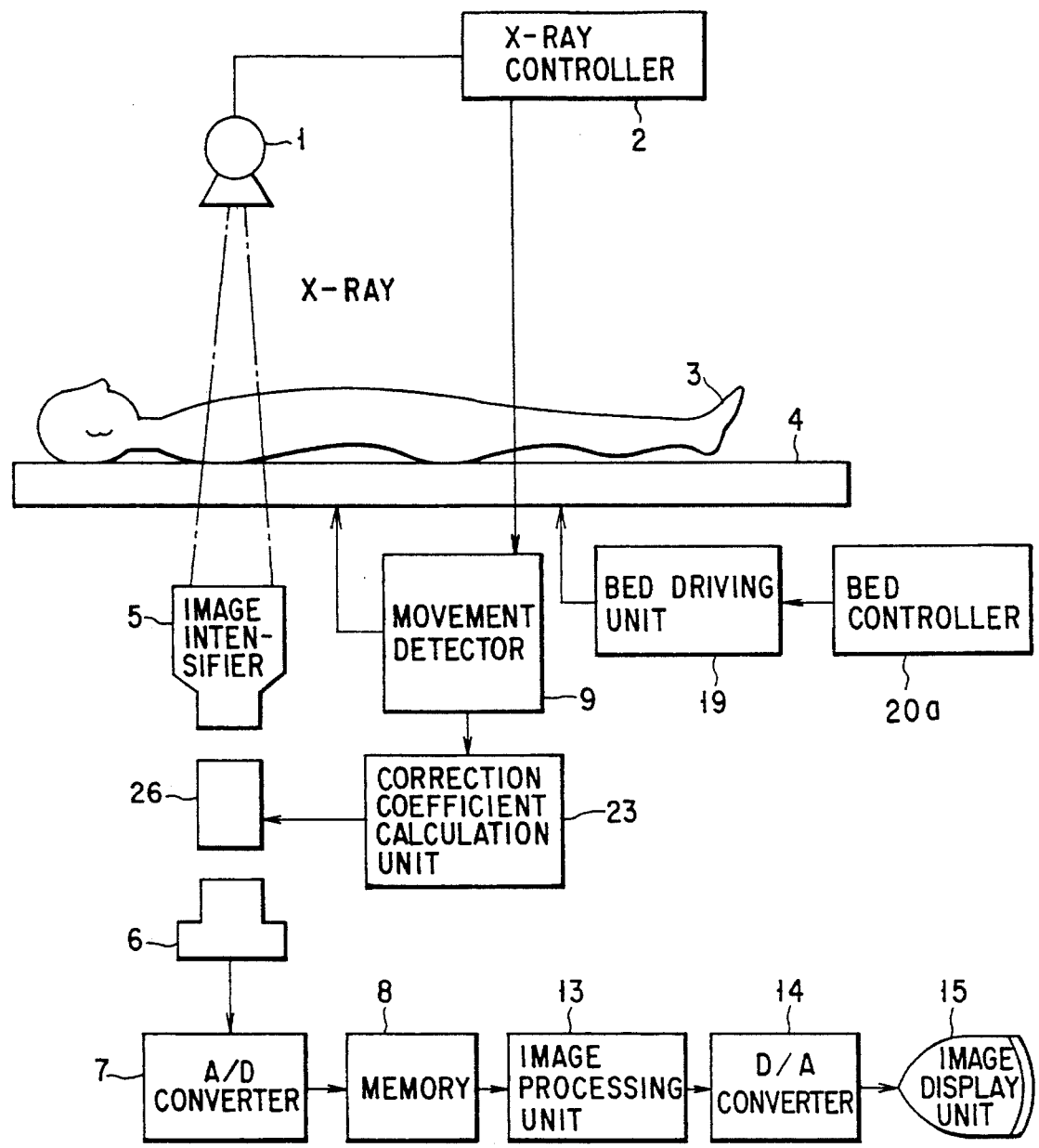
F I G. 10

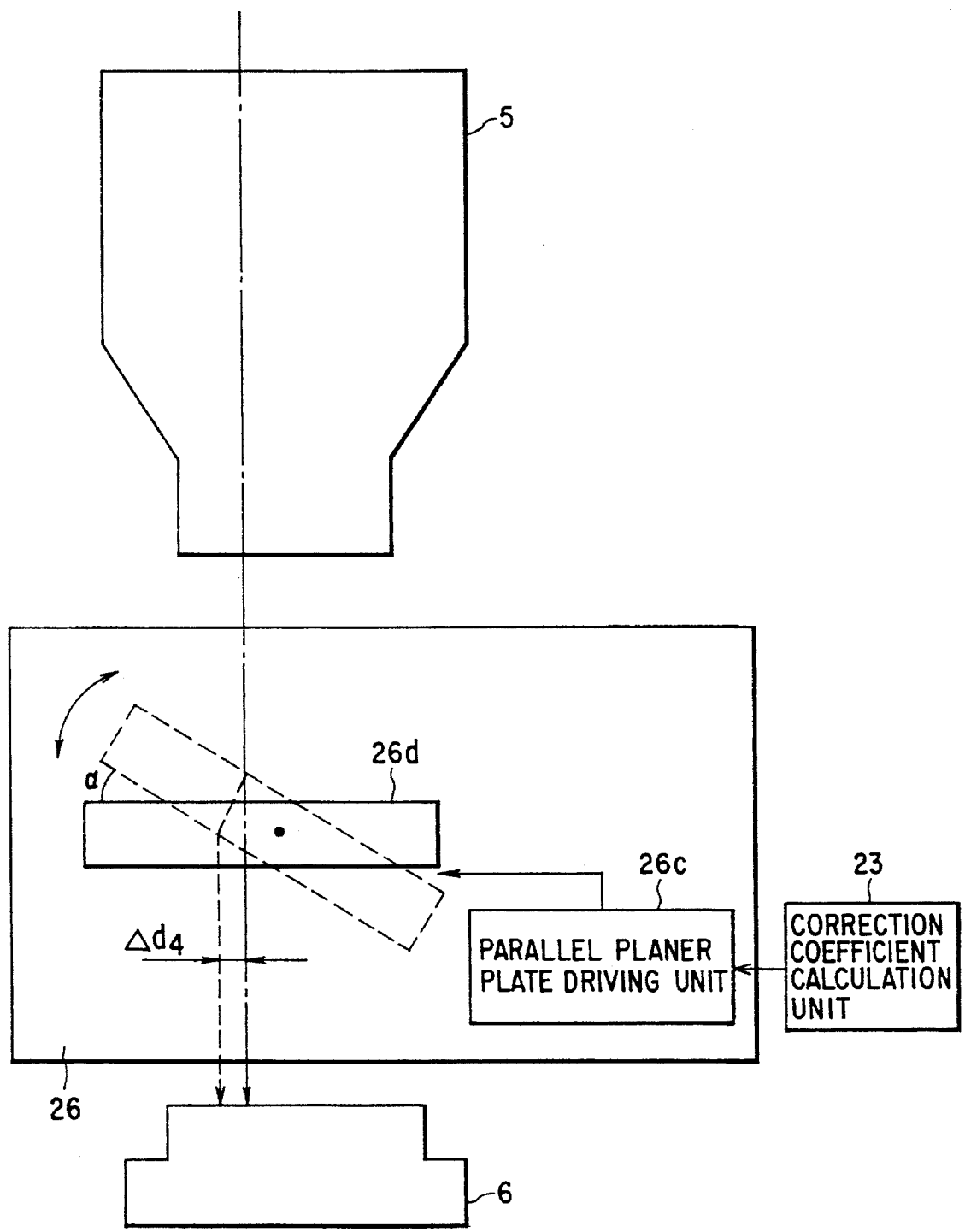
F I G. 12

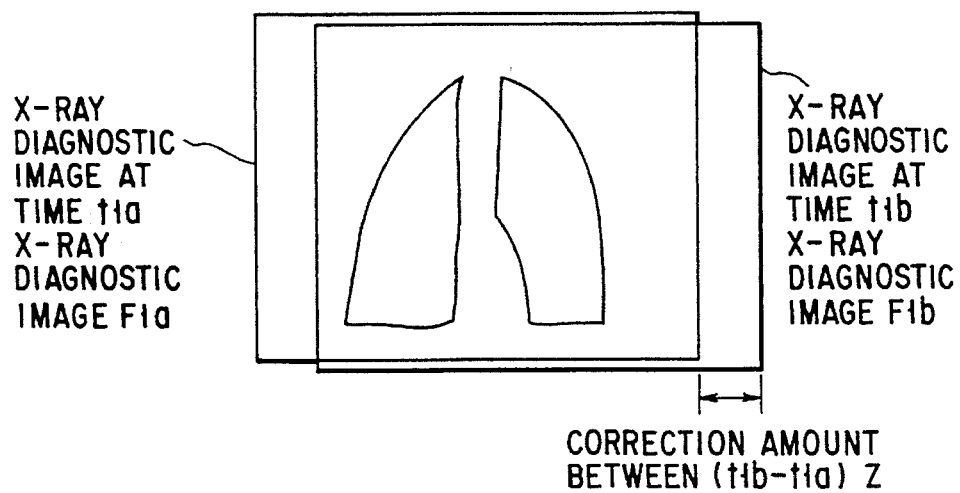
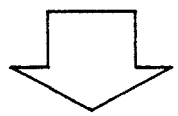
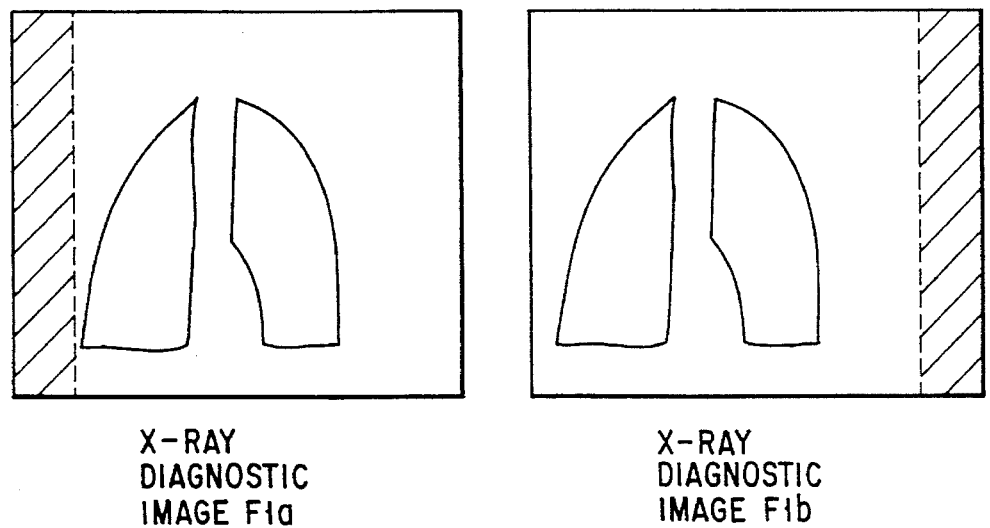
F I G. 18

X-RAY DIAGNOSIS APPARATUS

BACKGROUND OF THE INVENTION

1. Field of the Invention

The present invention relates to an X-ray diagnosis apparatus which diagnoses an object based on an X-ray diagnostic image of the object.

2. Description of the Related Art

An X-ray diagnosis apparatus which picks up a fluoroscopic image of a human body using X-rays or the like is known. This X-ray diagnosis apparatus is used to conduct angiography tests to observe the statuses of blood vessels in which a contrast medium has been injected. In the angiography tests, when an angiogram of a lower limb is taken, blood flows in a wide range should be traced in some case. In this case, a table moving pick-up scheme or the like is employed in which the X-ray tube and image intensifier system (hereinafter called "X-ray pick-up system") and an object are moved relative to each other to obtain angiograms.

FIG. 1 is a diagram showing the schematic structure of a conventional X-ray diagnosis apparatus. An X-ray tube 1 irradiates X-rays to an object 17 under the control of an X-ray controller 2. An image intensifier 5 converts X-rays passing through the object 17 into an optical image. A pick-up unit 6 (which is constituted of a CCD, for example) converts this optical image into a TV video signal, which is further converted into a digital signal by an A/D converter 7. The digital image signal is temporarily stored in an image memory 8, and is later output to an image processing unit 13 at a given timing. Digital image data which has undergone image adjustment processing in the image processing unit 13 is converted into a TV video signal by a D/A converter 14 and is displayed by an image display unit 15.

A supporter driving unit 18 moves a supporter 16 on which an X-ray pick-up system including the X-ray tube 1, image intensifier 5 and pick-up unit 6 (the supporter may hereinafter be simply called "X-ray pick-up system" sometimes) at a given speed in a predetermined direction. A bed driving unit 19 moves a bed at a given speed in a predetermined direction. A bed/supporter drive controller 20 controls the driving of the supporter driving unit 18 and the bed driving unit 19.

A description will be given of the occurrence of blurring of fluoroscopic images when the X-ray pick-up system (supporter 16) and the object 17 in the above structure moves relative to each other.

The table moving pick-up is executed while the bed driving unit 19 is driving the bed in response to a signal from the bed/supporter drive controller 20 during the irradiation of X-rays.

FIG. 2 shows the timing relation between an X-ray pulse and a collection image at the time of the conventional image collection.

The conventional X-ray diagnosis apparatus obtains a single X-ray fluoroscopic/pick-up image of an object (hereinafter simply called "X-ray diagnostic image") through a single irradiation. As shown in FIG. 2, a predetermined time T is needed as the time for a single irradiation (i.e., pulse width) to obtain a single X-ray diagnostic image. That is, an X-ray diagnostic image $F_1$ is obtained through irradiation at time $t_1$ and an X-ray diagnostic image $F_2$ is obtained through irradiation at time $t_2$. In this manner, a single X-ray diagnostic image $F_1, F_2, F_3, \ldots$ of the object is obtained through every irradiation. In this case, when the supporter 16 and the bed 4 move relative to each other (e.g., the bed 4 moves while the supporter 16 is fixed) during the time T equivalent to the X-ray pulse width, passed X-rays which include the movement of the object 17 due to the movement of the bed 4 are input to the image intensifier 5. As the resultant X-ray diagnostic image gradually shifts in accordance with the movement of the bed 4 during the irradiation of X-rays, blurring occurs in the obtained X-ray diagnostic image. This blurring is of the same type as the image blurring that occurs in the ordinary visible-rays based photographing due to the shaking of a camera.

The following methods may be employed to prevent the blurring of an X-ray diagnostic image from occurring due to the relative movement of the supporter 16 to the object 17.

The first method is to narrow the X-ray pulse width (i.e., to shorten the time T as much as possible). Simply narrowing the X-ray pulse width results in an insufficient dose of X-rays so that an image having the desired brightness and contrast cannot be obtained.

In this respect, the amplitude of the X-ray pulse (i.e., the amount of X-ray irradiation) is increased or the sensitivity of the X-ray detector is enhanced while making the X-ray pulse width narrower. Further, the image processing method may be improved. Since there are limits to the performance of the X-ray generator and/or the performance of the X-ray detector or the like, however, it is difficult to employ those methods.

As mentioned above, conventionally, when the X-ray pick-up system and the object move relative to each other, passed X-rays which include their relative movement are input to the image intensifier, thus causing the blurring of the resultant X-ray diagnostic image.

To reduce the dose of the X-ray irradiation for the X-ray fluoroscopy, the above-described X-ray diagnosis apparatus is normally combined with a digital fluorography device (hereinafter called "DF device") which can record images.

The DF device converts an X-ray diagnostic image obtained through the sequential irradiation of X-rays into image data consisting of digital signals to perform various image processes, and has advantages such that blood vessels with a low density can be displayed clearly and quantitative diagnosis is possible.

One of the image processes of the DF device performs is the automatic adjustment of the brightness and contrast of an image. This function is to temporarily input one frame of image data into a (frame) memory and automatically adjust the brightness and contrast or the like based on the image data within an area of interest (concerning area) designated by an operator or the like.

FIG. 3 shows one example of an X-ray diagnosis apparatus which employs such a DF device. Like or same reference numerals are used in FIG. 3 to denote components corresponding or identical to those shown in FIG. 1 and their detained descriptions will not be given again.

X-rays irradiated from the X-ray tube 1 pass through the object 17 and enter the image intensifier 5 where the X-rays are converted to optical image data. An X-ray limiter 3 adjusts the X-ray irradiation field.

The output data of the image intensifier 5 is converted into a TV video signal by the pick-up unit 6, which comprises a camera tube, solid state pick-up element or the like, and this TV video signal is further converted to digital image data by the A/D converter 7. The digital image data is output via the memory 8 to an adjustment coefficient calculation unit 21, which computes image adjustment coefficients, and the image processing unit 13, which executes image processing.

The output data of the A/D converter 7, which is temporarily stored in the memory 8, is read out together with data of a concerning area designated by the operator or the like, output from a concerning area designating unit 22, from the memory 8 by the adjustment coefficient calculation unit 21. This adjustment coefficient calculation unit 21 computes adjustment coefficients for the brightness and contrast of an image, for example, based on the image data corresponding to the designated concerning area, and outputs the adjustment coefficients to the image processing unit 13.

The image processing unit 13 has a memory 13a, an image processing circuit 13b and an image adjustment circuit 13c. The memory 13a temporarily stores the output data of the A/D converter 7. The image adjustment circuit 13c reads the image data, held in the memory 13a, via the image processing circuit 13b and performs the adjustment of the brightness and contrast on the read image data using the adjustment coefficients output from the adjustment coefficient calculation unit 21. The image data that has undergone the image adjustment is converted to a TV video signal by the D/A converter 14 and is then sent to the image display unit 15.

Using the adjustment coefficients obtained from the image data within the concerning area of the (N−1)-th frame image data, the image adjustment circuit 13c automatically performs an image adjustment process on the (N−1)-th frame of image data or the self image. The processed image data is thus sequentially displayed as an X-ray diagnostic image frame by frame by the image display unit 15.

If there is no memory 13a in FIG. 3, while the data flow is the same as the one described above, the image adjustment circuit 13c automatically performs an image adjustment on the N-th frame based on the image data within the concerning area of the (N−1)-th frame, using the adjustment coefficients which optimize the image within that concerning area.

The above-described conventional X-ray diagnosis apparatus has the memory 13a in the image processing unit 13 to determine adjustment coefficients using the memory 8 and the adjustment coefficient calculation unit 21 and perform an adjustment process on the image on which the adjustment coefficients have been determined (i.e., self image). Therefore, the fluoroscopic image displayed on the image display unit 15 is delayed by one frame from the fluoroscopic image that is collected at that point of time. When the operator inserts, for example, a catheter into a body while viewing the X-ray diagnostic image, the difference between the image of the actual manipulation and the displayed X-ray diagnostic image often gives awkward manipulation feeling to the operator.

If the memory 13a is eliminated to overcome the above problem, the memory 8 and the adjustment coefficient calculation unit 21 are used to calculate adjustment coefficients which optimize the (N−1)-th image based on the image data within the concerning area of the (N−1)-th frame and the actual image adjustment is executed on the N-th image. With this method, however, the brightness and contrast are inadequately adjusted when there are large changes in brightness and contrast between the images within the concerning areas of the (N−1)-th frame and the N-th frame particularly in the case where X-ray irradiation field is moved, for example, in the direction along the axis of the object 17 in response to drive signals from the supporter driving unit 18 that drives the supporter 16 on which the X-ray tube 1 and image intensifier 5 are mounted the and bed driving unit 19 that drives the bed 4.

Although the difference between the displayed X-ray diagnostic image and the image of the actual manipulation and the inadequate image adjustment are overcome if the image adjustment is not performed, the brightness/contrast of the X-ray diagnostic image is not adjusted, so that visibility and diagnosis may be affected.

SUMMARY OF THE INVENTION

Accordingly, it is a primary object of the present invention to provide an X-ray diagnosis apparatus which moves the X-ray pick-up system and an object relative to each other and reduces the blurring of an X-ray diagnostic image.

It is another object of this invention to provide an which can perform the adequate image adjustment process without frame delay even when the X-ray irradiation field is moved while image adjustment, such as the adjustment of brightness and contrast, is performed on a concerning area on the display screen.

An X-ray diagnosis apparatus according to the first aspect of the present invention is characterized by comprising: a bed on which an object is placed; supporting means on which X-ray irradiation means for irradiating a predetermined amount of X-rays to the object on the bed and converting means for converting X-rays passed through the object into an object image signal are mounted; first moving means for moving the bed; second moving means for moving the supporting means; and drive control means for controlling movement of at least the converting means in such a manner that the object appears to be stopped as viewed from the converting means while the bed and the supporting means are moved relative to each other by the first moving means and the second moving means and X-rays are irradiated from the X-ray irradiation means.

The drive control means includes means for controlling the second moving means. The apparatus further comprises first detecting means for detecting a moving direction and moving speed of the bed; and second detecting means for detecting a moving direction and moving speed of the supporting means; and wherein the converting means includes X-ray incident surface for receiving X-rays passed through the object, and the drive control means includes means for converting an amount of a change of the bed with respect to the supporting means during X-ray irradiation to an amount of a change on the X-ray incident surface of the converting means based on the moving directions and moving speeds detected by the first detecting means and the second detecting means, and controlling the second moving means in accordance with the change amount.

The apparatus further comprises third moving means for moving at least the converting means; and wherein the drive control means includes means for controlling the third moving means. In addition, the apparatus further comprises first detecting means for detecting a moving direction and moving speed of the bed; and second detecting means for detecting a moving direction and moving speed of the supporting means; and wherein the converting means includes X-ray incident surface for receiving X-rays passed through the object, and the drive control means includes means for converting an amount of a change of the bed with respect to the supporting means during X-ray irradiation to an amount of a change on the X-ray incident surface of the converting means based on the moving directions and moving speeds detected by the first detecting means and the second detecting means, and controlling the third moving means in accordance with the change amount. The drive control means includes means for multiplying an amount of a change of the bed to the supporting means during X-ray irradiation by a geometric magnification, obtained from a relative ratio of a distance from the X-ray irradiation means to the converting means to a distance from the object to the converting means, thereby obtaining an amount of a change the X-ray incident surface of the converting means.

The converting means includes: means for converting X-rays passed through the object to an optical image; and pick-up means for converting the optical image of the object into an image signal, and further comprising moving means for moving the pick-up means, wherein the drive control means includes means for controlling the fourth moving means. The apparatus further comprises first detecting means for detecting a moving direction and moving speed of the bed; and second detecting means for detecting a moving direction and moving speed of the supporting means; and wherein the converting means includes X-ray incident surface for receiving X-rays passed through the object, and the drive control means includes means for converting an amount of a change of the bed with respect to the supporting means during X-ray irradiation to an amount of a change the X-ray incident surface of the converting means based on the moving directions and moving speeds detected by the first detecting means and the second detecting means, and controlling the fourth moving means in accordance with the change amount. The drive control means includes means for multiplying an amount of a change of the bed to the supporting means during X-ray irradiation by a geometric magnification, obtained from a relative ratio of a distance from the X-ray irradiation means to the converting means to a distance from the object to the converting means, thereby obtaining an amount of a change on the X-ray incident surface of the converting means.

Another X-ray diagnosis apparatus according to the first aspect of the present invention is characterized by comprising: a bed on which an object is placed; supporting means on which X-ray irradiation means for irradiating a predetermined amount of X-rays to the object on the bed, converting means for converting X-rays passed through the object into an optical image, and pick-up means for converting the optical image into an image signal are mounted; first moving means for moving the bed; second moving means for moving the supporting means; and drive control means for controlling relative movement of the pick-up means to the converting means in such a manner that an image on a pick-up surface of the converting means is stopped while the bed and the supporting means are moved relative to each other by the first moving means and the second moving means and X-rays are irradiated from the X-ray irradiation means. The apparatus further comprises: first detecting means for detecting a moving direction and moving speed of the bed; and second detecting means for detecting a moving direction and moving speed of the supporting means; and wherein the converting means includes X-ray incident surface for receiving X-rays passed through the object, and the drive control means includes means for converting an amount of a change of the bed with respect to the supporting means during X-ray irradiation to an amount of a change on the X-ray incident surface of the converting means based on the moving directions and moving speeds detected by the first detecting means and the second detecting means, and controlling the second moving means in accordance with the change amount. The drive control means includes means for multiplying an amount of a change of the bed to the supporting means during X-ray irradiation by a geometric magnification, obtained from a relative ratio of a distance from the X-ray irradiation means to the converting means to a distance from the object to the converting means, thereby obtaining an amount of a change on the X-ray incident surface of the converting means.

Still another X-ray diagnosis apparatus according to the first aspect of the present invention is characterized by comprising: a bed on which an object is placed; supporting means on which X-ray irradiation means for irradiating a predetermined amount of X-rays to the object on the bed and converting means for converting X-rays passed through the object into an object image signal are mounted; moving means for moving the bed and the supporting means relative to each other; and optical path changing means for changing an optical path from the converting means to the supporting means in such a manner that an image on a pick-up surface of the converting means is stopped while the bed and the supporting means are moved relative to each other by the moving means and X-rays are irradiated from the X-ray irradiation means. The apparatus further comprises first detecting means for detecting a moving direction and moving speed of the bed; and second detecting means for detecting a moving direction and moving speed of the supporting means; and wherein the optical path changing means includes: a plate mirror inclined to an optical axis of output light from the converting means; mirror driving means for driving the mirror to make parallel movement in a same direction as a direction of relative movement of the bed to the supporting means; and control means for converting an amount of a change of the bed with respect to the supporting means during X-ray irradiation to an amount of a change on a light output surface of the converting means based on the moving directions and moving speeds detected by the first detecting means and the second detecting means, and controlling the mirror driving means in accordance with the change amount to make parallel movement of the mirror. The drive control means includes means for multiplying an amount of a change of the bed to the supporting means during X-ray irradiation by a geometric magnification, obtained from a relative ratio of a distance from the X-ray irradiation means to a distance from the object to the converting means and an optical magnification specific to the converting means, thereby obtaining an amount of a change on the light output surface of the converting means. The apparatus further comprises first detecting means for detecting a moving direction and moving speed of the bed; and second detecting means for detecting a moving direction and moving speed of the supporting means; and wherein the optical path changing means includes: a light transmittive, parallel planar plate supported rotatably with respect to a rotational axis perpendicular to an optical axis of output light from the converting means; parallel planar plate driving means for rotating the parallel planar plate in a same direction as a direction of relative movement of the bed to the supporting means; and control means for converting an amount of a change of the bed with respect to the supporting means during X-ray irradiation to an amount of a change on a light output surface of the converting means based on the moving directions and moving speeds detected by the first detecting means and the second detecting means, calculating a rotational angle of the parallel planar plate in accordance with the change amount, and controlling the parallel planar plate driving means to rotate the parallel planar plate by the rotational angle from a position perpendicular to the optical axis of the output light from the converting means. The apparatus further comprises first detecting means for detecting a moving direction and moving speed of the bed; and second detecting means for detecting a moving direction and moving speed of the supporting means; and wherein the optical path changing means includes: a plate mirror inclined to an optical axis of output light from the converting means; mirror driving means for rotating the mirror in accordance with a direction of relative movement of the bed to the supporting means; and control means for converting an amount of a change of the bed with respect to the supporting means during X-ray irradiation to an amount of a change on a light output surface of the converting means based on the moving directions and moving speeds detected by the first detecting means and the second detecting means, calculating a rotational angle of the mirror in accordance with the change amount, and controlling the mirror driving means to move the mirror by the rotational angle from a position perpendicular to the optical axis of the output light from the converting means. The apparatus further comprises first detecting means for detecting a moving direction and moving speed of the bed; and second detecting means for detecting a moving direction and moving speed of the supporting means; and wherein the optical path changing means includes: a prism located in a path of output light from the converting means; prism driving means for rotating the prism in a same direction as a direction of relative movement of the bed to the supporting means; and control means for converting an amount of a change of the bed with respect to the supporting means during X-ray irradiation to an amount of a change on a light output surface of the converting means based on the moving directions and moving speeds detected by the first detecting means and the second detecting means, calculating a rotational angle of the prism in accordance with the change amount, and controlling the prism driving means to rotate the prism by the rotational angle from a position perpendicular to the optical axis of the output light from the converting means.

According to the first aspect of this invention, the movement of the supporting means or the converting means is controlled in such a manner that the supporting means or converting means moves in the same direction and at the same speed as the bed during X-ray fluoroscopy/pick-up, so that the object appears to be stopped as viewed from the converting means. Therefore, the output light from the converting means does not move on the pick-up surface of the pick-up means, preventing image blurring.

An X-ray diagnosis apparatus according to the second aspect of this invention is characterized by comprising: a bed on which an object is placed; supporting means on which X-ray irradiation means for irradiating a predetermined amount of X-rays to the object on the bed and converting means for converting X-rays passed through the object into an object image signal are mounted; first moving means for moving the bed; second moving means for moving the supporting means; X-ray control means for controlling the X-ray irradiation means in such a way that at least two X-ray irradiations are executed in one period for obtaining a single image of the object; correction amount calculation means for correcting a moving direction and a moving mount for at least a single second image obtained through an X-ray irradiation following a first X-ray irradiation in the one period by relative movement between the bed and the supporting means in such a manner that the second image overlaps a first image obtained by the first X-ray irradiation in the one period; image correction means for correcting the second image in such a manner that the second image overlaps the first image based on the moving direction and moving amount for the second image, obtained by the correction calculation means; image adding means for adding the first image and the second image after correction; and image display means for displaying an image resulting from the addition. With the above structure, the X-ray irradiation means includes means for irradiating an X-ray pulse to the object with an X-ray pulse width for allowing a sum of irradiation times to provide a desired dose of X-rays and with an irradiation interval of the X-ray pulse equal to or longer than a time interval associated with transfer of accumulated charges on a light receiving surface of the converting means. Further, the X-ray irradiation means includes an X-ray limiter for preventing X-ray irradiation to a non-common area other than a portion where at least two images of the object, obtained by at least two irradiations, overlap.

According to the second aspect of this invention, at the time of X-ray fluoroscopy/pick-up, the amplitude of the X-ray pulse is set to the same as the one in the prior art and the pulse width is set to, for example, ½ of the conventional pulse width so that two X-ray irradiations are conducted in the conventional one frame period. The position of one of two images obtained in one frame period is corrected by moving pixels in accordance with the relative movement between the pick-up system and the object at the timings of two irradiations of X-ray pulses, in such a way that the position-corrected image overlaps the remaining image. Even if there is a relative movement between the pick-up system and the object at the time of X-ray irradiation in X-ray fluoroscopy/pick-up, therefore, the frame period is the same as the conventional one and the dose of X-rays does not become insufficient, thus providing an X-ray diagnostic image with reduced image noise and less motion blurring.

Further, as the width of the X-ray pulse is narrowed to reduce the motion blurring, the resolution of the X-ray diagnostic images is improved.

Since the necessity to stop the relative movement between the pick-up system and the object is reduced at the time X-rays are irradiated, the precision of reproducing the fluoroscopic position between a mask image and a contrast image is improved in the case of DSA (Digital Subtraction Angiography), for example.

In addition, since the X-ray limiter is used to prevent X-ray irradiation to a non-common area and to permit X-ray irradiation only to a common area according to the second aspect of this invention, the dose of the X-ray irradiation is reduced.

Since the necessity to stop the relative movement between the pick-up system and the object is reduced at the time of X-ray irradiation, the load on the system control and the mechanical load of stopping the movement are reduced.

An X-ray diagnosis apparatus according to the third aspect of this invention is characterized by comprising: X-ray irradiation means for irradiating X-rays toward a diagnosing portion of an object; converting means for converting X-rays passed through the object to image data; storage means for temporarily storing the image data, converted by the converting means, frame by frame; detecting means for detecting a moving direction and a moving speed of an irradiation field of the X-rays with respect to the object; designating means for designating a concerning area in the image data; area predicting means for predicting an area to be a concerning area in a next frame, based on detection values of the detecting means and the concerning area designated by the designating means; adjustment coefficient calculation means for calculating an image adjustment coefficient based on the image data in the storage means corresponding to the concerning area predicted by the area predicting means; image adjusting means for performing a desired image adjustment according to the image adjustment coefficient, calculated by the adjustment coefficient calculation means, on the image data converted by the converting means; and display means for displaying the image data having undergone the image adjustment. The image adjusting means includes means for adjusting at least one of brightness and contrast of an X-ray fluoroscopic image. The image adjusting means includes means for adjusting an output of the X-ray irradiation means based on the image adjustment coefficient.

According to the third aspect of this invention, X-rays irradiated from the X-ray irradiation means pass through the object and are then converted to image data. This image data (e.g., the (N−1)-th frame of image data) is temporarily stored in the storage means and is also supplied to the image adjusting means. In parallel to the supply of the image data, the area predicting means predicts an area on a current frame (e.g., (N−1)-th frame) of image data, temporarily stored in the storage means, which is expected to be a concerning area in the next frame (e.g., N-th frame), based on the moving direction and moving speed of the X-ray irradiation field with respect to the object, which are output from the detecting means, and the concerning area data output from the designating means. Based on the image data in the storage means corresponding to this predicted concerning area, the adjustment coefficient calculation means calculates an image adjustment coefficient for performing a desired image adjustment on the next frame (e.g., N-th frame) of image data.

Consequently, the image adjusting means can perform the desired image adjustment based on the given image adjustment coefficient (coefficient for the N-th frame of image data predicted from the (N−1)-th frame of image data) on the image data (N-th frame of image data) from the converting means. Alternatively, the output of the X-ray irradiation means may be changed based on the image adjustment coefficient to adjust the brightness and contrast of the X-ray diagnostic image.

According to the third aspect of this invention, as apparent from the above, when an X-ray diagnostic image is obtained by moving the X-ray irradiation field while executing an image adjustment process, such as the adjustment of brightness and contrast, the position of a concerning area in the next frame is predicted based on which the optimal image adjustment coefficient for that image adjustment for the next frame of image data is calculated from the current frame of image data, and the image adjustment is performed on the next frame using the calculated adjustment coefficient.

The use of the above-described method can eliminate a frame delay between the displayed X-ray diagnostic image and the image of the actual manipulation (e.g., the manipulation of a catheter while viewing the X-ray diagnostic image), thus eliminating a difference in operational feeling originated from such a frame delay. It is therefore possible for the operator to conduct the desired manipulation while viewing a high-quality X-ray diagnostic image. Particularly, there is a significant frame-delay oriented awkwardness according to the prior art when the irradiation field is moved, whereas the present invention surely eliminates such awkward feeling to reduce the burden on the operator, thus contributing to the improvement of the efficiencies of various works involved in the fluoroscopy.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 10 is a structural diagram of an X-ray diagnosis apparatus according to a third embodiment;

FIG. 12 is a diagram showing the internal structure of an optical correction unit according to a fourth embodiment;

FIG. 18 is a diagram showing X-ray irradiation with a non-common area masked in this invention;

DETAILED DESCRIPTION OF THE PREFERRED EMBODIMENTS

Preferred embodiments of the present invention will now be described referring to the accompanying drawings.

Figure 4:
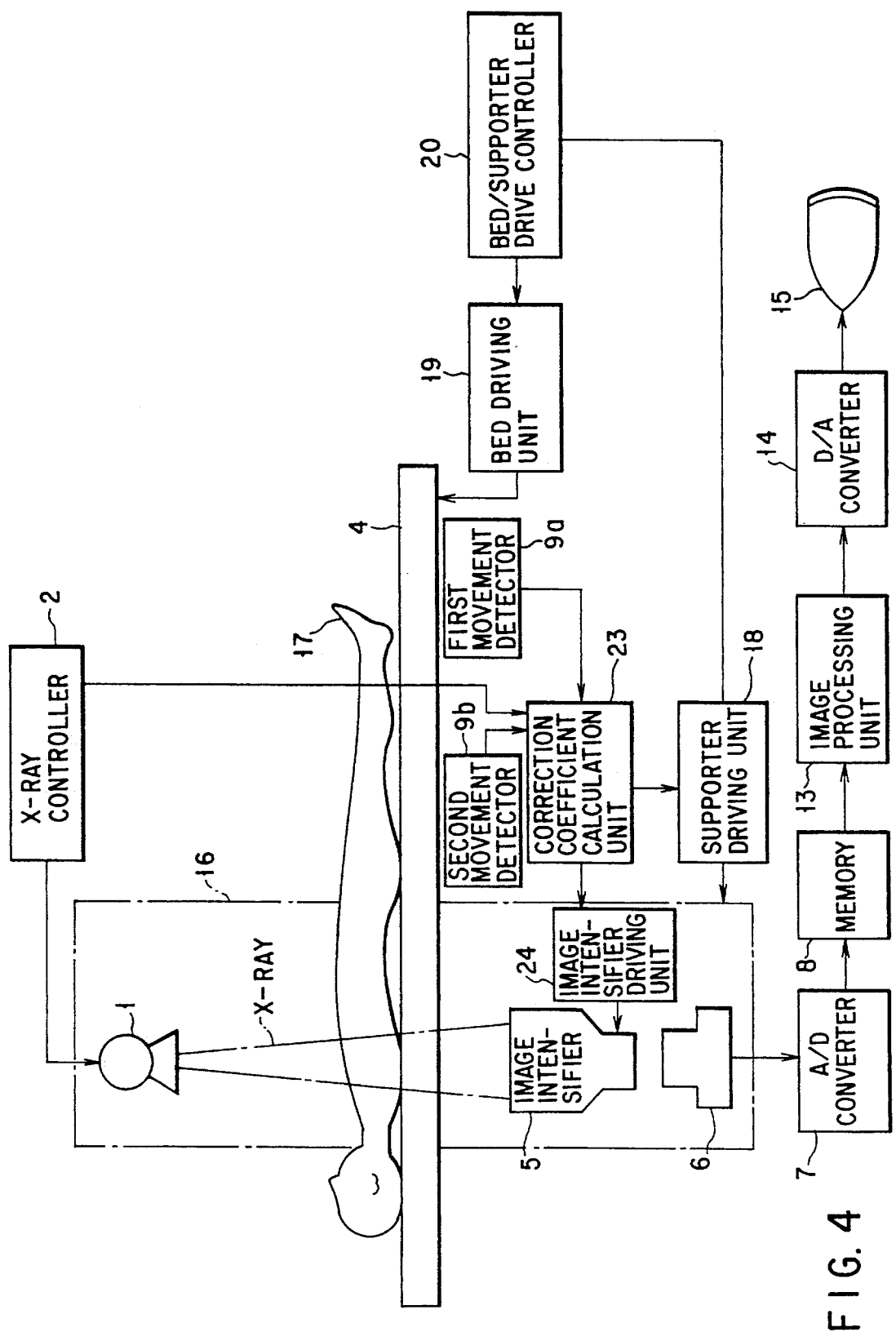
FIG. 4 is a block diagram showing the schematic structure of an X-ray diagnosis apparatus according to a first embodiment of the present invention.

FIG. 4 presents a block diagram showing the schematic structure of an X-ray diagnosis apparatus according to a first embodiment of the present invention.

This X-ray diagnosis apparatus comprises an X-ray tube 1, an X-ray controller 2, a bed 4, an image intensifier 5, a pick-up unit 6, an A/D converter 7, a memory 8, a first movement detector 9a, a second movement detector 9b, an image processing unit 13, a D/A converter 14, an image display unit 15, a supporter driving unit 18, a bed driving unit 19, a bed/supporter drive controller 20, a correction coefficient calculation unit 23, and an image intensifier driving unit 24.

The X-ray tube 1, image intensifier 5 and pick-up unit 6 are mounted on the supporter 16, and this supporter 16 and the bed 4 are movable independently of each other.

The X-ray tube 1 irradiates pulse X-rays to an object 17.

The X-ray controller 2 applies a pulse voltage the X-ray tube 1 to adjust the X-ray output from the X-ray tube 1.

The object 17 is placed on the bed 4.

The image intensifier 5 converts X-rays passed through the object 17 and bed 4 to an optical image and outputs the optical image to an unillustrated optical lens.

The pick-up unit 6, which may be a CCD camera, converts the optical image from the image intensifier 5 to a TV video signal.

The A/D converter 7 converts the TV video signal from the pick-up unit 6 to a digital signal.

The memory 8 temporarily stores the digital image signal.

The first movement detector 9a and second movement detector 9b respectively detect the moving directions and moving speeds of the supporter 16 and the bed 4.

The image processing unit 13 performs processing, such as a window process or affine transformation.

The D/A converter 14 converts the digital image, processed by the image processing unit 13, to an analog TV video signal.

The image display unit 15 displays the image signal that has been converted to the analog TV video signal.

The supporter driving unit 18 drives the supporter on which the X-ray pick-up system including the X-ray tube 1, image intensifier 5 and pick-up unit 6 is mounted, in a predetermined direction in parallel to the moving axis of the bed 4 (the long axis of the bed 4) and a predetermined speed.

The bed driving unit 19 drives the bed 4 in a predetermined direction in parallel to the long axis of the bed 4 (parallel to the long axis of the object 17) and a predetermined speed.

The bed/supporter drive controller 20 controls the driving of the supporter driving unit 18 and the bed driving unit 19.

The correction coefficient calculation unit 23 calculates and outputs such a correction coefficient as to eliminate the relative movement of the bed 4 to the image intensifier 5 or the supporter 6, based on the outputs of the first and second movement detectors 9a and 9b and the X-ray irradiation time during X-ray fluoroscopy/pick-up. The details of the calculation will be given later.

The image intensifier driving unit 24 drives the image intensifier 5 in parallel to the moving axis of the bed 4 (the long axis of the bed 4) independently of the supporter 16.

The function of the correction coefficient calculation unit 23 will now be described in detail.

The correction coefficient calculation unit 23 receives the moving speeds and moving directions of the supporter 16 and bed 4, detected by the first and second movement detectors 9a and 9b, and data on the application time of a tube voltage (i.e., data on the X-ray irradiation time) from the X-ray controller 2.

The calculation unit 23 converts a relative amount of a change (moving amount) $\Delta d_1$ between the bed 4 and the supporter 16 in the X-ray irradiation time (during irradiation) to the amount of a change $\Delta d_2$ on the X-ray incident surface of the image intensifier 5. This change $\Delta d_2$ is given by multiplying the change $\Delta d_1$ by a correction coefficient $\alpha$. The calculation unit 23 calculates the correction coefficient $\alpha$ prior to the conversion of the change $\Delta d_2$. The correction coefficient $\alpha$ is given as a geometric magnification based on the relative ratio of the distance from the X-ray tube 1 to the image intensifier 5 (generally called "SID") to the distance from the object 17 to the image intensifier 5 (generally called "PID"). The SID and PID are computed by the correction coefficient calculation unit 23 based on the vertical positions of the X-ray tube 1, the image intensifier 5 and the object 17, which are respectively supplied to an X-ray tube perpendicular moving mechanism, a supporter perpendicular moving mechanism and a bed perpendicular moving mechanism (none shown).

The correction coefficient calculation unit 23 controls the supporter driving unit 18 or the image intensifier driving unit 24 based on the change $\Delta d_2$ at the X-ray incident surface of the image intensifier 5. Accordingly, the image intensifier 5 is moved together with the optical lens and the pick-up unit 6 by the change $\Delta d_2$ relative to the bed 4 in the same direction as the relative moving direction of the bed 4 and supporter 16, during X-ray irradiation.

The operation of the thus constituted X-ray diagnosis apparatus according to the first embodiment will be discussed below.

There are following three cases possible when the bed 4 and the supporter 16 move (change) relative to each other. The first case is that the bed 4 moves with the supporter 16 unmoved. The second case is that the supporter 16 moves with the bed 4 unmoved. The third case is that the bed 4 and the supporter 16 both move. In the following description, it is assumed that the bed 4 moves while the supporter 16 is unmoved (first case) for the sake of convenience.

Figure 5:
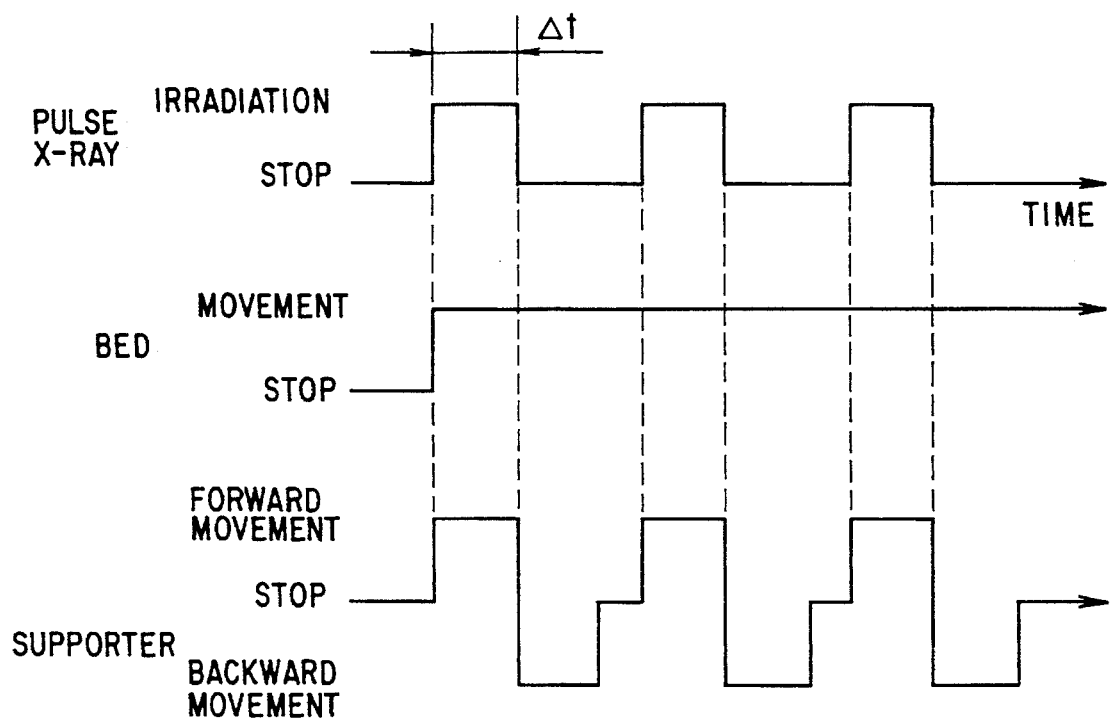
FIG. 5 is a time chart illustrating the operation of the first embodiment.
Figure 9:
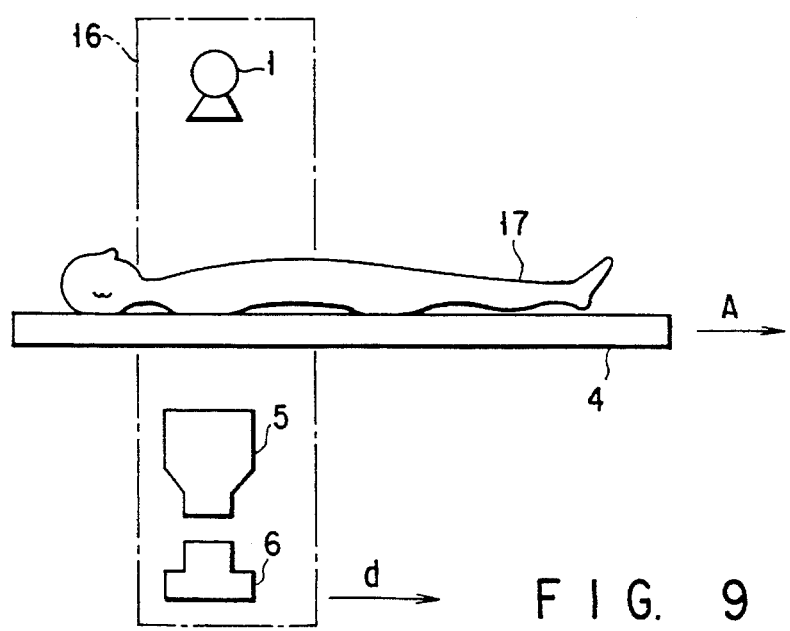
FIG. 9 is a diagram showing the moving direction of a pick-up unit when a bed and a supporter move relative to each other.
Figure 6:
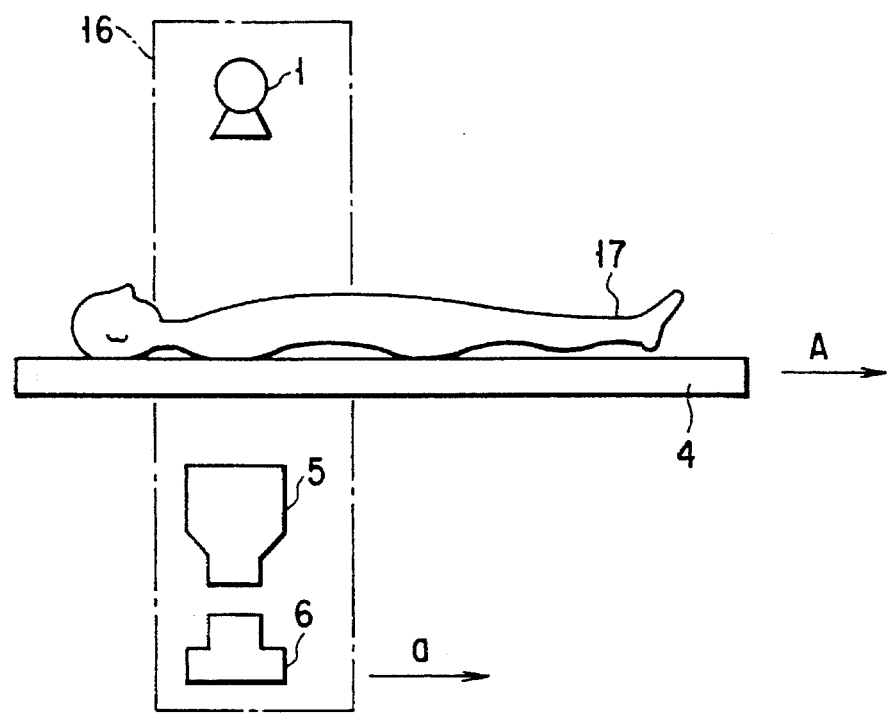
FIG. 6 is a diagram showing the moving direction of an image intensifier when a bed and a supporter move relative to each other.

FIG. 5 is a time chart illustrating the moving timing of the supporter 16. FIG. 6 is a diagram showing the moving direction of the image intensifier 5 when the bed 4 and the supporter 16 move relative to each other.

As shown in FIG. 6, the bed 4 is driven by the bed driving unit 19 to continuously move in the direction of the arrow A at a constant speed. When X-ray fluoroscopy starts, a voltage with a given pulse width is repeatedly applied to the X-ray tube 1 in a given period by the X-ray controller 2. Accordingly, X-rays are repeatedly irradiated from the X-ray tube 1 toward the object 17 placed on the bed 4. The X-ray irradiation time $\Delta t$ is constant according to the pulse width.

The pick-up unit 6 repeats the pick-up operation in synchronism with the X-ray irradiation period. More specifically, the pick-up unit 6 performs charge accumulation while the X-rays are irradiated, and reads signal charges while the X-ray irradiation is stopped.

The correction coefficient calculation unit 23 calculates a correction coefficient α equivalent to a geometric magnification, based on the relative ratio of the distance from the X-ray tube 1 to the image intensifier 5 (generally called "SID") to the distance from the object 17 to the image intensifier 5 (generally called "PID"), and holds the result.

The moving direction and moving speed of the bed 4, detected by the first movement detector 9a, are sent to the correction coefficient calculation unit 23. The calculation unit 23 calculates the amount of a change (moving amount) $\Delta d_1$ of the bed 4 during a single X-ray irradiation based on the detected moving direction and moving speed of the bed 4 and the X-ray irradiation time (i.e., the pulse width), and multiplies the change $\Delta d_1$ by the correction coefficient α to obtain the amount of a change $\Delta d_2$ on the X-ray incident surface of the image intensifier 5.

Based on this change $\Delta d_2$, the calculation unit 23 outputs signals to control the supporter driving unit 18 and the image intensifier driving unit 24.

In the case where the supporter 16 is moved by the supporter driving unit 18, the driving unit 18 moves the supporter 16 by the change $\Delta d_2$ in the same direction a as the moving direction of the bed 4 during X-ray irradiation. More specifically, the supporter 16 starts moving from a predetermined position at the beginning of the X-ray irradiation (hereinafter called "reference position (initial position)") in the same direction a as the bed 4 and at a predetermined speed, in such a manner that the supporter 16 reaches a position apart from the reference position by the change $\Delta d_2$ at the end of the irradiation.

When the X-ray irradiation ends, the supporter driving unit 18 moves the supporter 16 in the opposite direction to the direction a back to the reference position until the next X-ray irradiation starts.

In the case where the image intensifier 5 is moved by the image intensifier driving unit 24, the correction coefficient calculation unit 23 outputs a signal to control the image intensifier driving unit 24 based on the change $\Delta d_2$ on the X-ray incident surface of the image intensifier 5. Under this control, the image intensifier driving unit 24 moves the image intensifier 5 together with the optical lens and the pick-up unit 6 by the change $\Delta d_2$ in the same direction a as the moving direction of the bed 4 during X-ray irradiation. More specifically, as in the case of moving the supporter 16, the image intensifier 5 starts moving from a reference position (initial position) at the beginning of the X-ray irradiation in the same direction a as the moving direction of the bed 4, in such a manner that the image intensifier 5 reaches a position apart from the reference position by the change $\Delta d_2$ at the end of the irradiation. When the X-ray irradiation ends, the image intensifier driving unit 24 moves the image intensifier 5 in the opposite direction to the direction a back to the reference position until the next X-ray irradiation starts.

Figure 7:
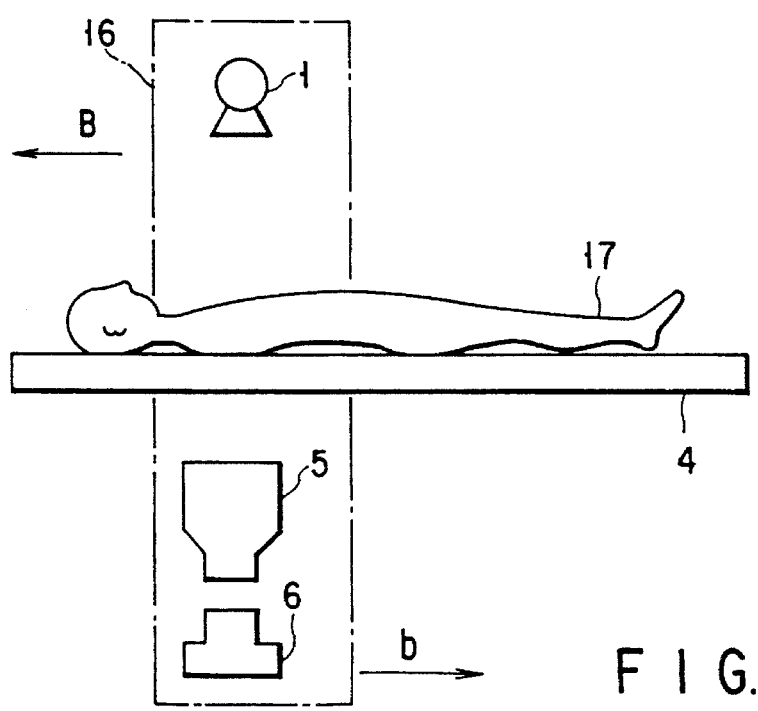
FIG. 7 is a diagram showing another moving direction of the image intensifier when the bed and supporter move relative to each other.

In the case where the supporter 16 moves in the direction of the arrow B with the bed 4 stopped as shown in FIG. 7, the image intensifier 5 moves by the change $\Delta d_2$ in the opposite direction b to the moving direction of the supporter 16 during X-ray irradiation.

According to this embodiment, as described above, as the supporter 16 or the image intensifier 5 (including the pick-up unit 6) follows up the movement of the bed 4, the object 17 appears to be stopped as viewed from the image intensifier 5 and the pick-up unit 6, thus preventing the X-ray diagnostic image from being blurred.

To prevent image blurring, the bed 4 may be intermittently moved in synchronism with the X-ray irradiation. While this approach can prevent the image blurring in principle, it is difficult to control the driving of the bed 4 to ensure accurate intermittent movement of the bed 4 regardless of a variation in weight of objects. In addition, the X-ray diagnostic image is blurred as the object 17 fluctuates due to the intermittent movement of the bed 4.

The X-ray diagnosis apparatus according to the first embodiment does not have those shortcomings.

Figure 8:
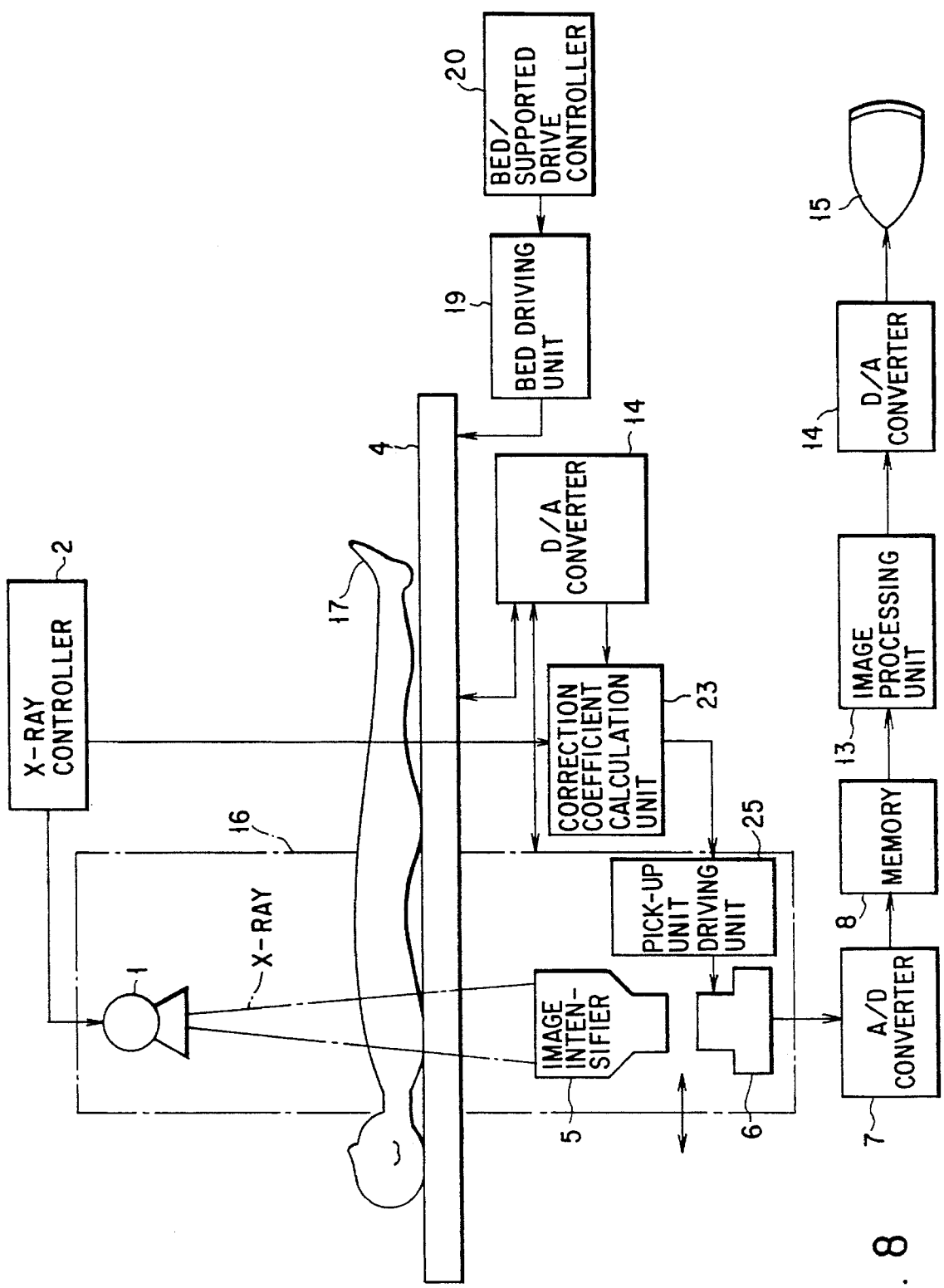
FIG. 8 is a structural diagram of an X-ray diagnosis apparatus according to a second embodiment.

FIG. 8 is a block diagram showing the schematic structure of an X-ray diagnosis apparatus according to a second embodiment of this invention. Like or same reference numerals are used in FIG. 8 to denote components corresponding or identical to those shown in FIG. 4 to avoid repeating their detained descriptions. FIG. 8 shows the embodiment in which only the pick-up unit 6 is moved in accordance with the movement of the bed 4.

The X-ray tube 1 and the image intensifier 5 are secured to the supporter 16. The pick-up unit 6 is arranged on the light output side of the image intensifier 5 via an unillustrated optical lens. A pick-up unit driving unit 25 drives the pick-up unit 6 in a direction parallel to the moving axis of the bed 4 (long axis of the bed 4) independently of the supporter 16.

The correction coefficient calculation unit 23 receives the relative moving speed and moving direction between the supporter 16 and bed 4, detected by the first and second movement detectors 9a and 9b. The calculation unit 23 also receives data on the application time of a tube voltage, i.e., data on the X-ray irradiation time, from the X-ray controller 2.

The calculation unit 23 converts a relative amount of a change (moving amount) $\Delta d_1$ between the bed 4 and the supporter 16 in the X-ray irradiation time (during irradiation) to the amount of a change $\Delta d_3$ on the pick-up surface (light receiving surface) of the pick-up unit 6. This change $\Delta d_3$ is given by multiplying the change $\Delta d_1$ by a correction coefficient β. The calculation unit 23 calculates the correction coefficient β prior to the conversion of the change $\Delta d_3$. The correction coefficient β is given by multiplying a geometric magnification based on the relative ratio of the distance from the X-ray tube 1 to the image intensifier 5 (generally called "SID") to the distance from the object 17 to the image intensifier 5 (generally called "PID"), by an optical magnification specific to the image intensifier 5 and an optical magnification specific to the optical lens.

The correction coefficient calculation unit 23 controls the pick-up unit driving unit 25 based on the change $\Delta d_3$. Accordingly, the pick-up unit 6 is moved by the change $\Delta d_3$ in the same direction (arrow d) as the relative moving direction (arrow A) of the bed 4 and supporter 16 during X-ray irradiation, independently of the supporter 16 and the image intensifier 5.

According to the second embodiment, as described above, since the pick-up unit 6 follows up the movement of the bed 4, the object 17 appears to be stopped as viewed from the pick-up unit 6, thus preventing the X-ray diagnostic image from being blurred as per the first embodiment. Further, the second embodiment unlike the first embodiment has only to move the pick-up unit 6, so that the pick-up unit driving unit 25 requires smaller driving power as compared with the driving power needed in the first embodiment. This allows the apparatus of the second embodiment to be designed more compact.

FIG. 10 is a block diagram showing the schematic structure of an X-ray diagnosis apparatus according to a third embodiment of this invention. Like or same reference numerals are used in FIG. 10 to denote components corresponding or identical to those shown in FIG. 4 to avoid repeating their detained descriptions. The third embodiment is designed to prevent an X-ray diagnostic image from being blurred by the movement of an optical system.

Figure 11:
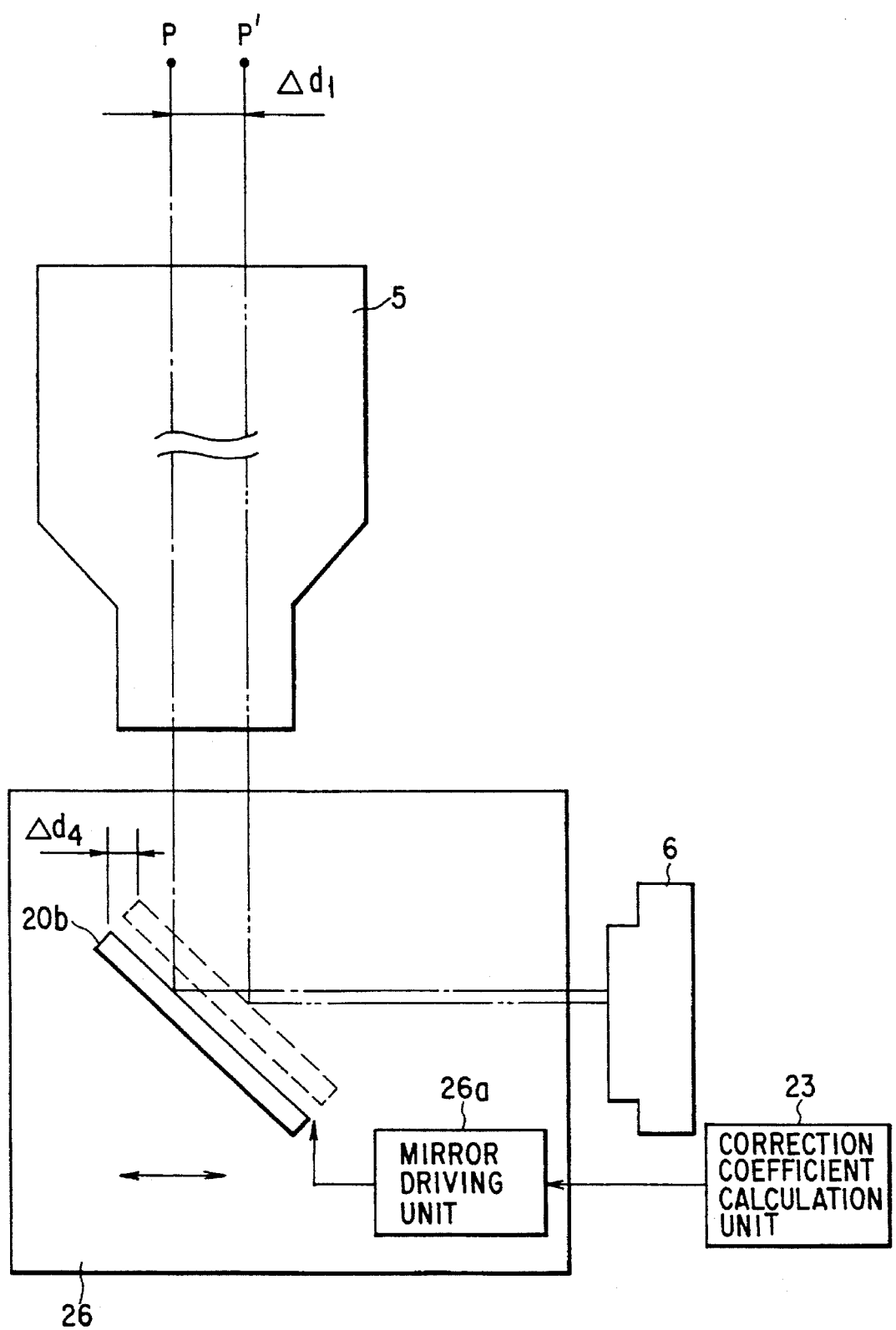
FIG. 11 is a diagram showing the internal structure of an optical correction unit in FIG. 10.

The X-ray tube 1 and the image intensifier 5 are secured to the supporter 16. The pick-up unit 6 is supported on the supporter 16 on the light output side of the image intensifier 5 via an optical correction unit 26. FIG. 11 is a diagram exemplifying the internal structure of the optical correction unit 26. Disposed in the optical correction unit 26 is a plate mirror 26b inclined at a predetermined angle (45 degrees) with respect to the optical axis of the output light from the image intensifier 5. The output light of the image intensifier 5 is reflected at the mirror 26b to enter the pick-up surface (light receiving surface) of the pick-up unit 6. A mirror driving unit 26a moves the mirror 26b in a direction parallel to the moving axis of the bed 4 (lengthwise direction of the bed 4).

The correction coefficient calculation unit 23 receives the relative moving speed and moving direction between the supporter 16 and bed 4, detected by a movement detector 9. The calculation unit 23 also receives data on the application time of a tube voltage (i.e., data on the X-ray irradiation time) from the X-ray controller 2. The calculation unit 23 converts a relative amount of a change (moving amount) $\Delta d_1$ between the bed 4 and the supporter 16 during X-ray irradiation to the amount of a change $\Delta d_4$ on the light output surface of the image intensifier 5. This change $\Delta d_4$ is given by multiplying the change $\Delta d_1$ by a correction coefficient $\gamma$. The calculation unit 23 calculates the correction coefficient $\gamma$ prior to the conversion of the change $\Delta d_4$. The correction coefficient $\gamma$ is given by multiplying a geometric magnification based on the relative ratio of the distance from the X-ray tube 1 to the image intensifier 5 (generally called "SID") to the distance from the object 17 to the image intensifier 5 (generally called "PID"), by an optical magnification specific to the image intensifier 5.

The correction coefficient calculation unit 23 controls the mirror driving unit 26a based on the change $\Delta d_4$. Accordingly, the mirror 26b is moved by the change $\Delta d_4$ in the same direction as the relative moving direction of the bed 4 and supporter 16 during X-ray irradiation, as indicated by the broken line in FIG. 11. Even when the bed 4 and the supporter 16 move relative to each other, therefore, the optical image does not move on the pick-up surface of the pick-up unit 6 so that no blurring of the X-ray diagnostic image occurs as per the first embodiment. As the output light of the image intensifier 5 is projected in parallel to the pick-up surface of the pick-up unit 6 via the mirror 26b, the X-ray diagnostic image is not deformed even when the mirror 26b moves. Further, the third embodiment has only to move the mirror 26b, so that the mirror driving unit 26a requires smaller driving power as compared with the driving power needed in the first embodiment or the second embodiment. This allows the apparatus of the third embodiment to be designed more compact.

A fourth embodiment will now be discussed. The fourth embodiment differs from the third embodiment only in the optical correction unit, and the other components are the same. The structure of the X-ray diagnosis apparatus of the fourth embodiment will not therefore be illustrated. FIG. 12 is a diagram showing the internal schematic structure of the optical correction unit 26 which is the essential portion of the fourth embodiment. Like or same reference numerals are used in FIG. 12 to denote components corresponding or identical to those shown in FIG. 11 to avoid repeating their detained descriptions.

A light-transmittive, parallel planar plate 26d, like an acrylic plate or a glass plate, which has a different index of refraction (refraction factor) from that of the air therearound, is disposed in the optical correction unit 26 to be rotatable around the rotational axis perpendicular to the optical axis of the output light of the image intensifier 5. When the parallel planar plate 26d is at a horizontal position (hereinafter called "0 degree position") perpendicular to the optical axis of the output light of the image intensifier 5, the output light from the image intensifier 5 passes through the parallel planar plate 26d and enters straight the pick-up surface (light receiving surface) of the pick-up unit 6. When the parallel planar plate 26d is rotated by a parallel planar plate driving unit 26c from the 0 degree position to a position inclined by an inclination angle $\alpha_0$ to the optical axis of the output light of the image intensifier 5, the output light from the image intensifier 5 reflects at the incident point and output point of the parallel planar plate 26d and moves in parallel by the distance $\Delta d_4$ corresponding to the inclination angle $\alpha_0$ to enter the pick-up surface (light receiving surface) of the pick-up unit 6.

The correction coefficient calculation unit 23 receives the relative moving speed and moving direction between the supporter 16 and bed 4, detected by a movement detector 9. The calculation unit 23 also receives data on the application time of a tube voltage, i.e., data on the X-ray irradiation time, from the X-ray controller 2. The calculation unit 23 converts a relative amount of a change (moving amount) $\Delta d_1$ between the bed 4 and the supporter 16 in the X-ray irradiation time (during X-ray irradiation) to the amount of a change $\Delta d_4$ on the light output surface of the image intensifier 5. This change $\Delta d_4$ is given by multiplying the change $\Delta d_1$ by a correction coefficient $\gamma$, as per the third embodiment. The calculation unit 23 calculates the correction coefficient $\gamma$ prior to the conversion of the change $\Delta d_4$. The correction coefficient $\gamma$ is given by multiplying a geometric magnification based on the relative ratio of the distance from the X-ray tube 1 to the image intensifier 5 (generally called "SID") to the distance from the object 17 to the image intensifier 5 (generally called "PID"), by an optical magnification specific to the image intensifier 5.

Further, the correction coefficient calculation unit 23 calculates the rotational angle $\alpha_0$ of the parallel planar plate 26d based on the change $\Delta d_4$, and controls the parallel planar plate driving unit 26c in such a way that the parallel planar plate 26d rotates by the rotational angle $\alpha_0$. Accordingly, the parallel planar plate 26d rotates by the rotational angle $\alpha_0$ from the 0 degree position in the direction according to the relative moving direction between the bed 4 and the supporter 16. Even when the bed 4 and the supporter 16 move relative to each other, therefore, the optical image does not move on the pick-up surface of the pick-up unit 6 and no blurring of the X-ray diagnostic image occurs.

Figure 13:
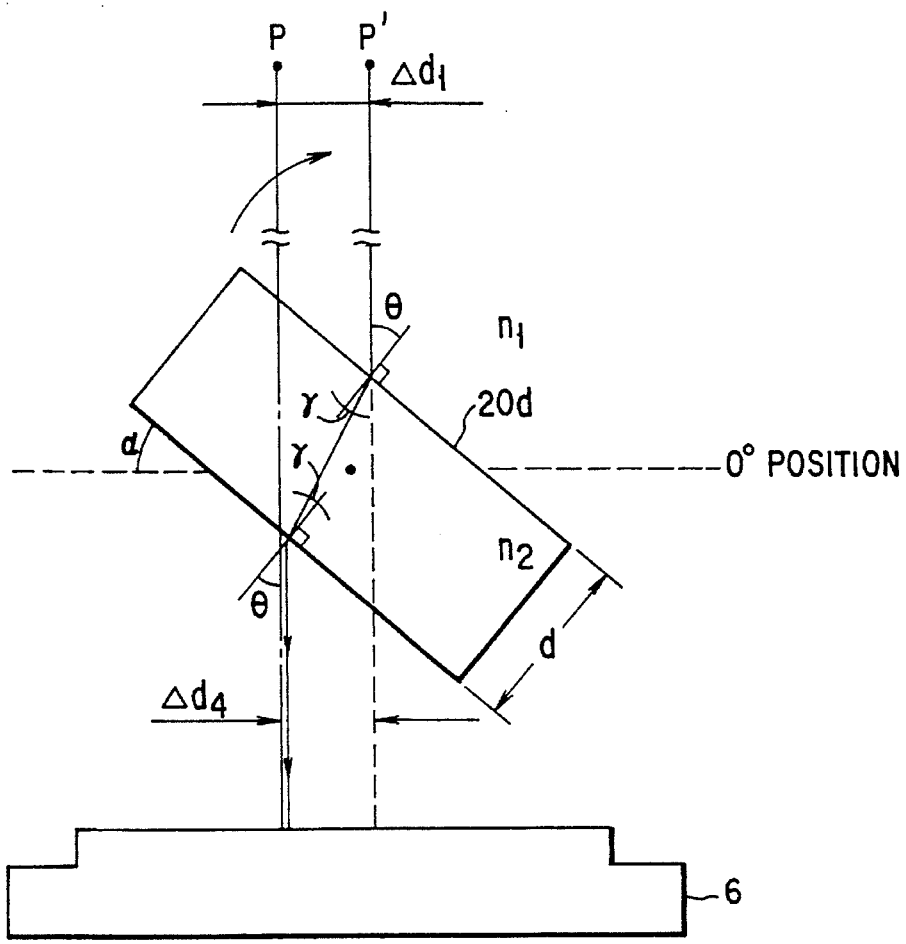
FIG. 13 is a diagram for explaining how to calculate the rotational angle of a parallel planar plate in FIG. 12.

The rotational angle $\alpha_0$ is obtained from the change $\Delta d_4$ in the following manner. FIG. 13 is a diagram for explaining how to calculate the rotational angle. Provided that $n_1$ is the air refraction factor, $n_2$ is the refraction factor of the parallel planar plate 26d, d is the thickness of the plate 26d, d' is the light-transmittive length in the plate 26d, $\theta$ is the incident angle to the plate 26d, and $\gamma$ is the angle defined by the internal transmittive optical axis of the plate 26de and the line normal to the plate 26d, then $$\theta = \alpha \qquad (1)$$

$$\cos \gamma = d/d' \quad (2)$$

Rewriting the equation (2) yields $$d' = d/\cos \gamma \quad (3)$$

From the refraction theory, $$n_1 \times \sin \theta = n_2 \times \sin \gamma \quad (4)$$

From the equations (1) and (2), we obtain $$\gamma = \sin^{-1}((n_1 \times \sin \alpha)/n_2) \quad (5)$$

With the position of the parallel planar plate 26d taken as the origin, $$\begin{aligned} \Delta d_4 &= d' \times \sin(\theta - \gamma) \\ &= (d \times \sin(\theta - \gamma))/\cos\gamma \end{aligned} \quad (6)$$

Substituting the equation (5) into the equation (6) yields $$\Delta d_4 = d' \times \sin(\alpha - \sin^{-1}(n_1 \times \sin \alpha)/n_2))/(\cos(\sin^{-1}(n_1 \times \sin \alpha)/n_2) \quad (7)$$

Based on the equation (7), the rotational angle $\alpha_0$ is calculated from the change $\Delta d_4$. For example, with d=5 mm, $\alpha$ becomes 1 degree, 2 degrees, 3 degrees, 4 degrees, 10 degrees and 20 degrees for $\Delta d_4$=29 μm, 58 μm, 87 μm, 116 μm, 294 μm and 609 μm, respectively.

As mentioned above, the parallel planar plate 26d is rotated by the rotational angle $\alpha_0$ corresponding to the change $\Delta d_4$ according to the relative moving direction between the bed 4 and supporter 16 during X-ray irradiation. Even when the bed 4 and the supporter 16 move relative to each other, therefore, the optical image does not move on the pick-up surface of the pick-up unit 6 so that no blurring of the X-ray diagnostic image occurs. As the output light of the image intensifier 5 is projected in parallel to the pick-up surface of the pick-up unit 6 via the parallel planar plate 26d, the X-ray diagnostic image is not deformed even when the plate 26d moves. Further, since it is sufficient to move the plate 26d, the parallel planar plate driving unit 26c requires smaller driving power as compared with the driving power needed in the first embodiment or the second embodiment. This allows the apparatus of the fourth embodiment to be designed more compact.

Figures 14, 15:
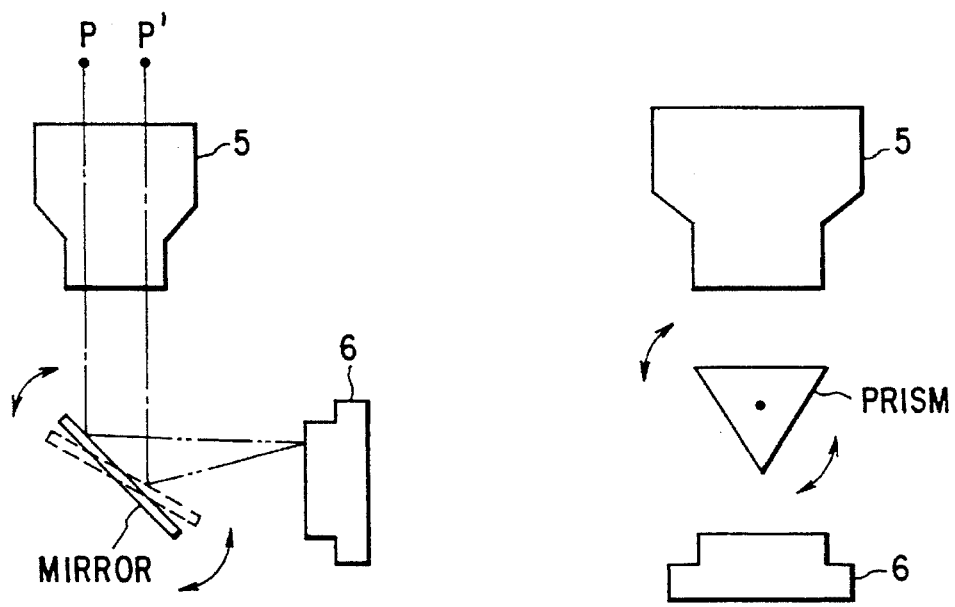
FIG. 14 is a diagram showing a first modification of the optical correction unit.
FIG. 15 is a diagram showing a second modification of the optical correction unit.

In the fourth embodiment, a plate mirror may be provided to be rotatable around the rotational axis perpendicular to the optical axis of the output light of the image intensifier 5 as shown in FIG. 14, or a light-transmittive prism with a triangular cross section, like an acrylic plate or a glass plate, which has a different index of refraction (refraction factor) from that of the air therearound, may be provided to be rotatable around the rotational axis perpendicular to the optical axis of the output light of the image intensifier 5 as shown in FIG. 15. The structures shown in FIGS. 14 and 15 however cause slight deformation of an X-ray diagnostic image.

Figure 16:
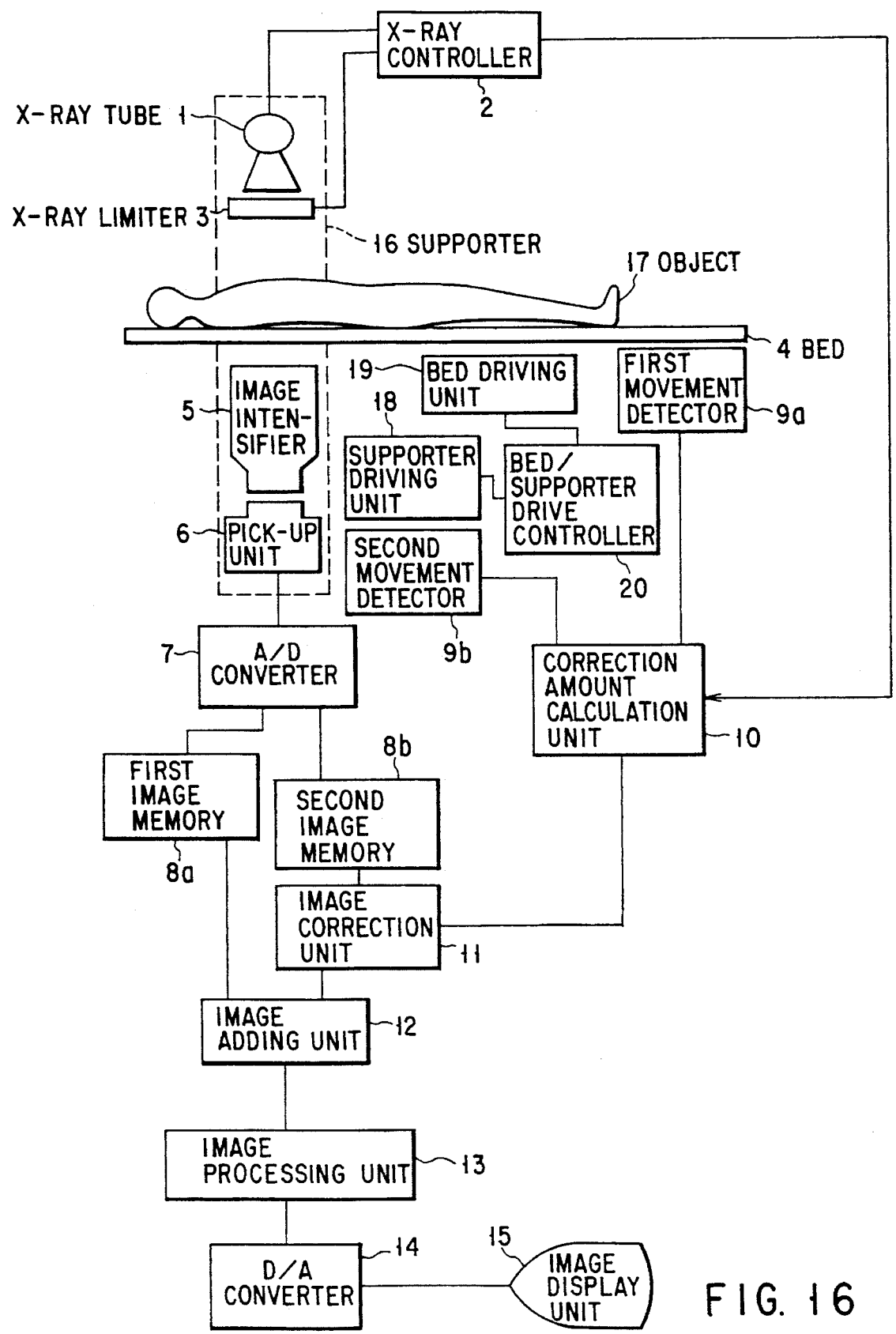
FIG. 16 is a block diagram showing the schematic structure of an X-ray diagnosis apparatus according to a fifth embodiment of this invention.

FIG. 16 is a block diagram showing the schematic structure of an X-ray diagnosis apparatus according to a fifth embodiment of this invention. Like or same reference numerals are used in FIG. 16 to denote components corresponding or identical to those shown in FIG. 4 to avoid repeating their detained descriptions.

In the X-ray diagnosis apparatus according to the fifth embodiment, the bed on which the object is placed and the X-ray pick-up system move relative to each other, the width of the X-ray pulse in one image collection time is narrowed, X-rays are irradiated a plurality of times, and the amount of movement is corrected for each irradiation, thereby reducing image blurring. In this case, if the width of the X-ray pulse is ½ of the normal pulse width in a single irradiation, when the irradiation is performed twice, the fluctuation of the X-ray diagnostic image caused by the relative movement of the bed (or the X-ray pick-up system) during the X-ray irradiation becomes a half, so that the image blurring is reduced. The following description will be given of the case where the X-ray pulse width is set to ½ of the ordinary pulse width and the irradiation is carried out twice, for the sake of convenience.

A first image memory 8a and a second image memory 8b temporarily store digital image signals. The first image memory 8a temporarily stores the image obtained through the first irradiation, and the second image memory 8b temporarily stores the image obtained through the second irradiation.

The first movement detector 9a and second movement detector 9b respectively detect the moving directions and moving speeds of the supporter 16 and the bed 4.

A correction amount calculation unit 10 calculates the correction value for the movement of the image obtained through the second irradiation, based on the output values of the first and second movement detectors 9a and 9b and the X-ray pulse length value output from the X-ray controller 2.

An image correction unit 11 corrects the position of the image obtained through the second irradiation, based on the image temporarily stored in the second image memory 8b and the movement correction value output from the correction amount calculation unit 10.

An image adding unit 12 adds the image in the first image memory 8a and the output image from the image correction unit 11.

The operation of the thus constituted X-ray diagnosis apparatus of this embodiment will be described below with reference to FIGS. 16 and 17. In the following description, a CCD camera is used as the pick-up unit 6 and a frame transfer (FT) system is used with the progressive scanning as the CCD driving system.

When there is a relative movement between the supporter 16 and the object 17, generally, one can consider narrowing the X-ray pulse width to suppress the image blurring. However, simply narrowing the X-ray pulse width results in an insufficient dose of X-rays. The dose of X-rays may be increased (the amplitude of the X-ray pulse is increased) in association with the shortened X-ray pulse length T. This approaches requires a large-capacity X-ray generator and is not thus practical. According to this invention, in this respect, the pulse width is set to ½ of the conventional one, irradiation is executed twice in association with the reduced pulse width, and the images obtained through the two irradiations are added together to reduce the image blurring while the performance of the conventional X-ray diagnosis apparatus is maintained.

Figure 1:
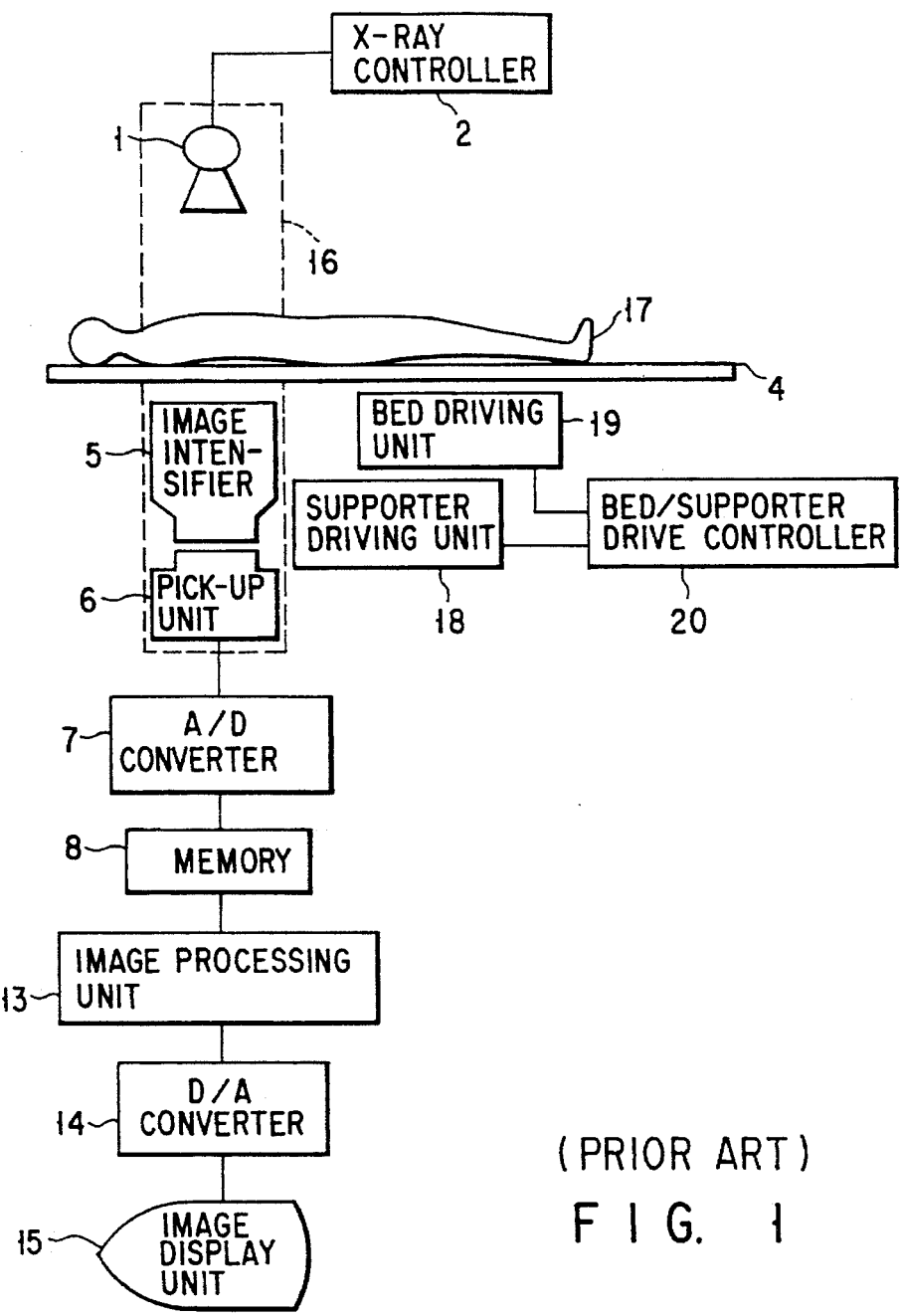
FIG. 1 is a diagram showing the schematic structure of a conventional X-ray diagnosis apparatus.

For example, in the conventional X-ray diagnosis apparatus shown in FIGS. 1 and 2, an X-ray pulse of a time length T is irradiated once in one period $T_C$ (hereinafter called "one frame period" for the sake of convenience). In this case, a single X-ray diagnostic image ($F_1, F_2, F_3, \ldots$) of the object is obtained for each frame period $T_C$.

Figure 17:
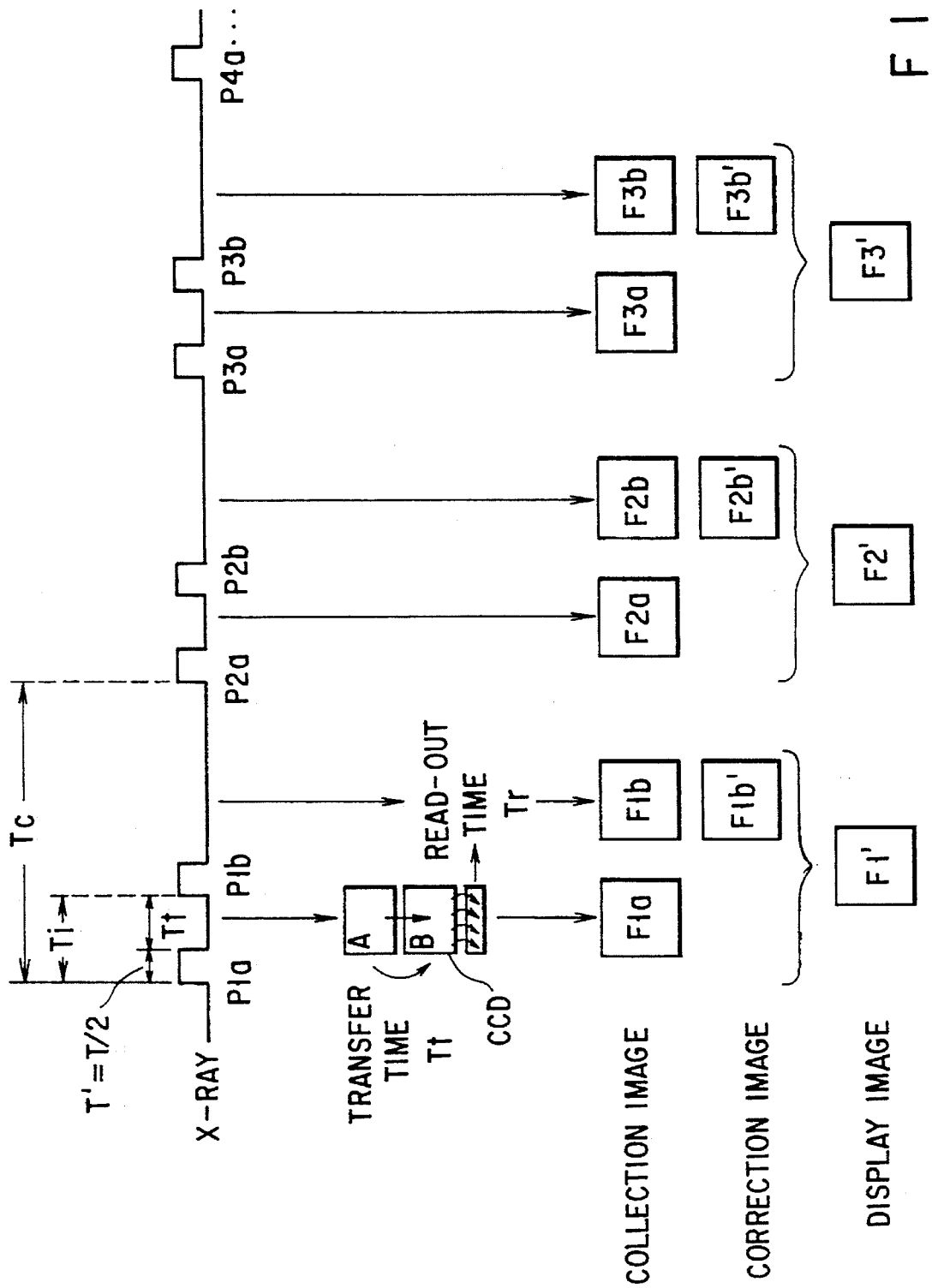
FIG. 17 is an exemplary diagram of an FT (Frame Transfer) type CCD driving system adapted to this invention.

In the fifth embodiment, the X-ray controller 2 controls the X-ray tube 1 to set the time length T' of the X-ray pulse from the X-ray tube 11 to a half of the conventional pulse width T (i.e., T/2) as shown in FIG. 17 and set the time $T_i$ to the next pulse generation equal to the sum of the frame transfer time $T_t$ (to be described later) in the FT type CCD driving system and the pulse width T' (=T/2), i.e., $T_t + T/2$, and two X-ray irradiations are performed in one frame period. The number of the X-ray irradiations is not limited to two. According to this invention, the pulse width of the X-ray pulse may be narrowed as much as the performance of the CCD permits. This can reduce the blurring of an X-ray diagnostic image caused by the relative movement between the supporter 16 and the object 17 during X-ray irradiation.

The X-rays, which have been irradiated under the above condition and have passed the object 17 and the bed 4 during the relative movement of the supporter 16 to object 17, enter the image intensifier 5 to be converted into visible rays. The visible rays enter the pick-up unit 6 via the optical system.

Then, X-ray diagnostic images $F_{1a}$ and $F_{1b}$ are obtained from X-ray pulses $P_{1a}$ and $P_{1b}$. The X-ray diagnostic images output from the pick-up unit 6 are converted into digital signals by the A/D converter 7, and the X-ray diagnostic images $F_{1a}$ and $F_{1b}$ are respectively input to the first image memory 8a and the second image memory 8b.

The first movement detector 9a and the second movement detector 9b detect the moving directions and moving speeds of the bed 4 and the supporter 16, and output those values to the correction amount calculation unit 10. The X-ray controller 2 outputs the repeat time $T_i$ for the irradiation of the X-ray pulse to the calculation unit 10.

The calculation unit 10 predicts the positional deviation between the X-ray diagnostic image $F_{1a}$ and the X-ray diagnostic image $F_{1b}$, obtained after the elapse of the repeat time $T_i$ while the supporter 16 and object 17 were moving relative to each other, as a length (i.e., the number of pixels) to calculate the movement correction value Z for the X-ray diagnostic image $F_{1b}$ with respect to the X-ray diagnostic image $F_{1a}$, and outputs the length to the image correction unit 11. The correction amount calculation unit 10 previously predicts a non-common area between the X-ray diagnostic images $F_{1a}$ and $F_{1b}$ (i.e., the portion where both X-ray diagnostic images do not overlap each other) based on this movement correction value Z, as shown in FIG. 18, and outputs the calculation result to the X-ray controller 2. As the X-ray controller 2 inserts the X-ray limiter 3 in the non-common area at the time of X-ray irradiation, thus reducing the amount of the X-ray irradiation.

The X-ray diagnostic image $F_{1a}$ stored in the first image memory 8a is output directly to the image adding unit 12, and the X-ray diagnostic image $F_{1b}$ stored in the second image memory 8b is output to the image correction unit 11. The image correction unit 11 performs positional correction in such a way that the collection time for the X-ray diagnostic image $F_{1b}$ becomes equivalent to the collection time for the X-ray diagnostic image $F_{1a}$ (e.g., the parallel movement of the pixels), and outputs the ray diagnostic image $F_{1b}'$ after the positional correction to the image adding unit 12. The image adding unit 12 adds the pixel values of the X-ray diagnostic images $F_{1b}$ and the collection time for the X-ray diagnostic image $F_{1b}'$ to produce the X-ray diagnostic image $F_1$.

The above procedures will be discussed more specifically with reference to FIG. 18. Suppose that the collection time for the X-ray diagnostic image $F_{1a}$ has started at time $t_{1a}$ and the collection time for the X-ray diagnostic image $F_{1b}$ has started at time $t_{1b}$ in FIG. 18.

The correction amount calculation unit 10 calculates the amount of the movement of the image of the object 17 on the receiving surface of the pick-up unit 6 from the relative moving direction and moving speed between the supporter 16 and object 17 at the repeat time $T_i=(t_{1b}-t_{1a})$ for the irradiation of the X-ray pulse. As the X-ray diagnostic image $F_{1a}$ can be considered as a reference, the calculation unit 10 corrects the amount of the relative movement between the supporter 16 and the object 17 at the repeat time $T_i$ for the irradiation of the X-ray pulse, with respect to the X-ray diagnostic image $F_{1b}$, to yield an X-ray diagnostic image $F_{1b}'$. The collection time for the X-ray diagnostic image $F_{1b}'$ can therefore be considered as the pseudo time for the time $t_{1a}$ at which the collection of the X-ray diagnostic image has actually started. In FIG. 18, the shaded portion is where the X-ray diagnostic image $F_{1a}$ and X-ray diagnostic image $F_{1b}$ do not overlap each other, and is a non-common area that is not used in diagnosis, so that no X-ray irradiation is necessary for this area. By controlling the X-ray limiter 3 by the X-ray controller 2 to avoid irradiation to this portion, therefore, the amount of X-ray irradiation can be reduced.

Thereafter, X-ray diagnostic images $F_2'$, $F_3'$, . . . are obtained at the interval $T_C$ in quite the same procedures as described above.

Figure 2:
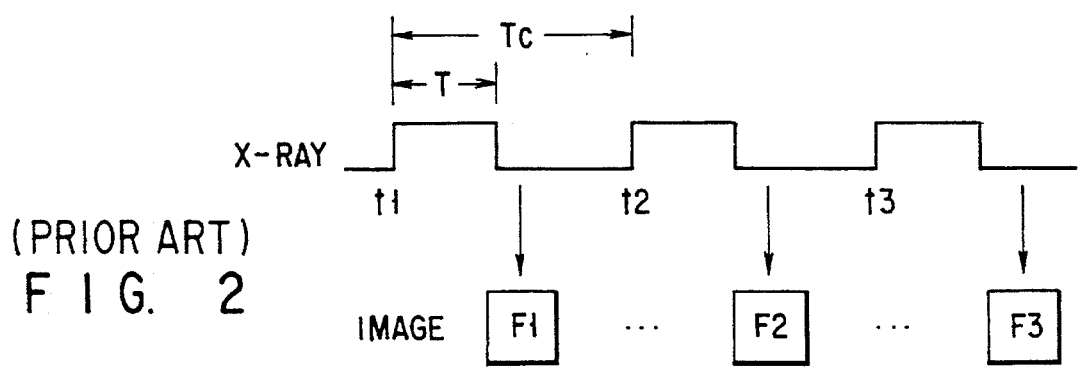
FIG. 2 is a diagram showing the timing relation between an X-ray pulse and a collection image at the time of the conventional image collection.

The X-ray diagnostic images $F_1'$, $F_2'$, $F_3'$, and so forth, obtained in the above manner by the fifth embodiment will be compared with the X-ray diagnostic images $F_1$, $F_2$, $F_3$, and so forth, which are obtained by the conventional method illustrated in FIG. 2.

A single X-ray diagnostic image is obtained in one frame period $T_C$ in both the fifth embodiment of this invention and the prior art. However, the amount of X-rays irradiated per X-ray diagnostic image in this invention is smaller because no X-ray irradiation is performed to the non-common area of the two X-ray diagnostic images that are to be overlapped. In the case where irradiation is executed twice, the X-ray pulse width for the X-ray diagnostic image $F_1'$ in this invention is ½ of the conventional one, so that the amount of blurring caused by the relative movement between the supporter 16 and the object 17 in the X-ray irradiation time to a half. Although the X-ray diagnostic image $F_{1a}$ and the X-ray diagnostic image $F_{1b}$ are obtained by two X-ray irradiations in one frame period $T_C$ and are added together to yield the X-ray diagnostic image $F_1'$, The positional deviation between the fluoroscopic X-ray diagnostic images $F_{1a}$ and $F_{1b}$ due to different collection times raises no problem because $F_{1b}$ is corrected to $F_{1b}'$ as described above.

Since two X-ray diagnostic images are added to obtain a single X-ray diagnostic image in the fifth embodiment, noise on this X-ray diagnostic image is reduced as compared with a single X-ray diagnostic image that is obtained by an X-ray pulse having the same amplitude and same width.

Although the use of the progressive scanning and frame transfer (FT) system as the CCD driving system for the pick-up unit 6 is the premise in the fifth embodiment, another similar driving system, such as a frame interline transfer (FIT) system, may also be employed.

The FT system will now be explained. FIG. 17 is an explanatory diagram of the FT type CCD driving system.

In the diagram, the X-ray pulse width T' is the time for a single X-ray irradiation, the repeat time for the irradiation of the X-ray pulse, $T_i$, is the time from the start of one X-ray pulse $P_{1a}$ to the start of the next X-ray pulse $P_{1b}$, the time $T_C$ is one frame period (cycle time for obtaining a single X-ray diagnostic image as a consequence), the transfer time $T_t$ is the time for the transfer of the accumulated charges of the CCD (frame transfer), and the image signal read-out time $T_r$ is the time for reading out the X-ray diagnostic image signal.

In the FT system, the light receiving surface of the CCD is only the surface A. After X-ray irradiation, the accumulated charges on the entire surface A are transferred to the surface B with the frame transfer time $T_t$. Thereafter, the image signals (or charges) on the surface B are sequentially read scanning line by scanning line, and data of the entire surface B is read out with the image signal read-out time $T_r$. This FT system has an advantage such that when the accumulated charges on the surface A are transferred to the surface B, the next X-ray irradiation can be performed on the surface A immediately. That is, the X-ray irradiation repeat time $T_1$ depends on the frame transfer time $T_t$ of the CCD, and X-rays can be irradiated at the interval $T_i$ which satisfies $$T_i \geq T_t + T_r.$$

If conditions $T_C \geq 2(T_t + T_r)$ and $T_r \leq T' + T_t$ are satisfied, two X-ray irradiations are possible in one frame period $T_C$ in which case two X-ray diagnostic images can be obtained in that period.

The minimizing $T_i$ that is determined by the CCD performance is advantageous in that the movement correction value Z can be small.

An X-ray diagnosis apparatus according to a sixth embodiment of this invention will now be described with reference to FIGS. 19 through 20B.

Figure 19:
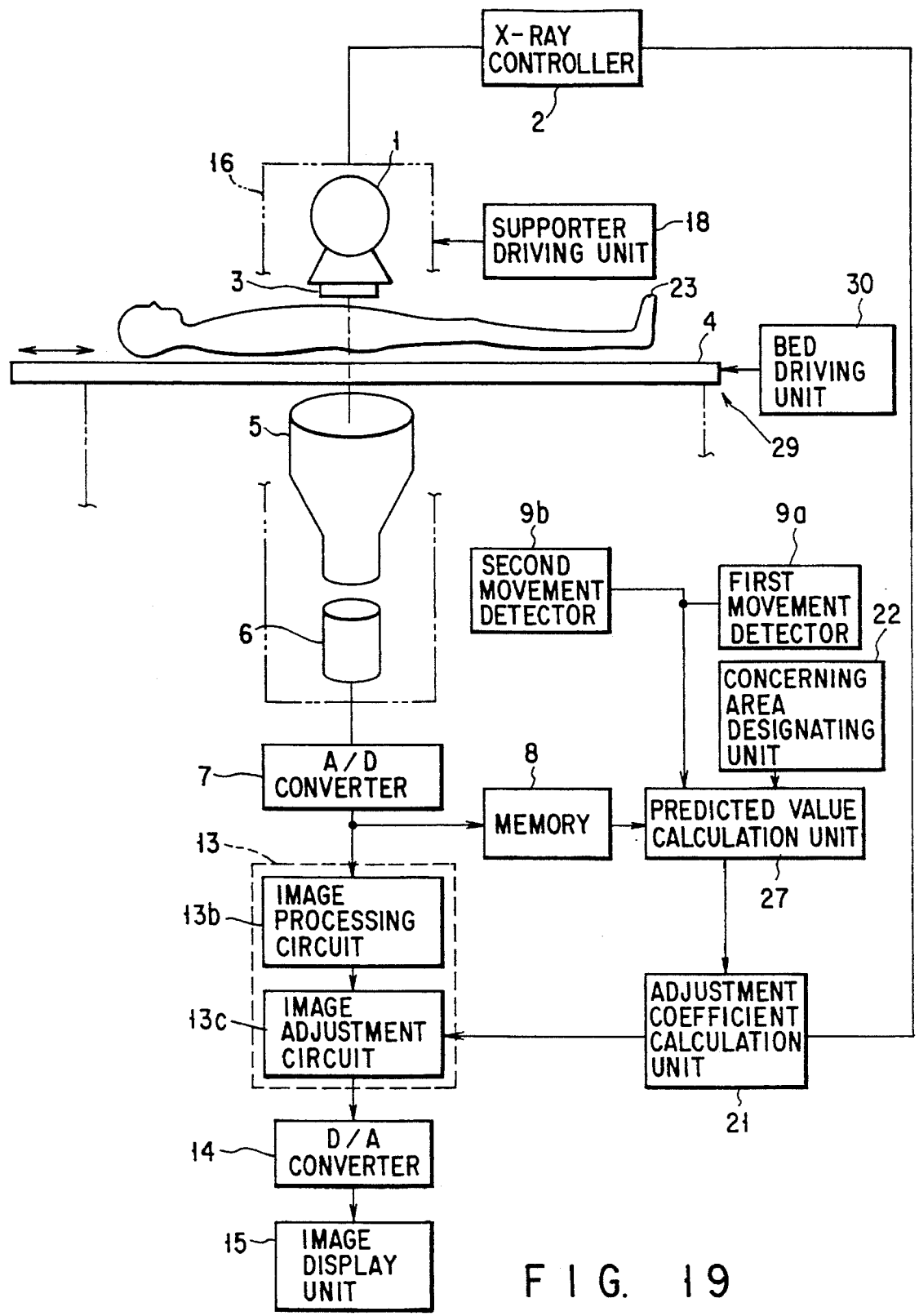
FIG. 19 is a block diagram showing the schematic structure of an X-ray diagnosis apparatus according to a sixth embodiment of this invention.

FIG. 19 is a block diagram showing the schematic structure of the X-ray diagnosis apparatus according to the sixth embodiment. Like or same reference numerals are used in FIG. 19 to denote components corresponding or identical to those shown in the diagrams that have already been discussed to avoid repeating their detained descriptions.

In FIG. 19, connected to the pick-up unit 6 is an A/D converter 7 whose conversion output is separated into two. One output is sent to an image processing unit 13, which performs image processing on an X-ray diagnostic image and automatically adjusts the brightness and contrast. The other output is sent via a memory 8 to a predicted value calculation unit 27, which calculates an adjustment coefficient to adjust at least one of the brightness and contrast of the X-ray diagnostic image.

The memory 8 has a memory area corresponding to one frame of image data received, and stores digital image data converted by the A/D converter 7 frame by frame.

Connected to the predicted value calculation unit 27 is a concerning area designating unit 22 which designates a desired area in the frame image data as a concerning area based on designation data input by the operator. The predicted value calculation unit 27 reads out image data from the memory 8 at every given timing, and receives the data on the concerning area designated by the concerning area designating unit 22 and the detection signals from first and second movement detectors 9a and 9b. The calculation unit 27 predicts an area on the image data, stored in the memory 8 when the X-ray irradiation field has been moved, which area becomes a concerning area for the next frame.

The image data of the concerning area predicted by the predicted value calculation unit 27 is sent to an adjustment coefficient calculation unit 21, which calculates an adjustment coefficient to optimize the adjustment of the brightness and contrast. This adjustment coefficient is sent to the image processing unit 13.

The image processing unit 13 loads the image data, converted by the A/D converter 7, to an image adjustment circuit 13c via an image processing circuit 13b. The image adjustment circuit 13c performs brightness and contrast adjustment processes for each pixel, such as the multiplication of each image data by the adjustment coefficient given then by the adjustment coefficient calculation unit 21.

The image data, undergone the image adjustment by the image adjustment circuit 13c, is sent via a D/A converter 14 to an image display unit 15. As a result, the image data is converted to a TV video signal by the D/A converter 14, and is then displayed as an X-ray diagnostic image on the image display unit 15.

The description of the operation of the X-ray diagnosis apparatus according to the sixth embodiment will be given below and will be centered on the prediction and calculation by the predicted value calculation unit 27.

Pulse X-rays are irradiated from the X-ray tube 1 at every given timing, and the X-rays associated with this irradiation pass through the object 17 and enter the image intensifier 5. The image intensifier 5 converts the received X-ray projection image into an optical image for each fluoroscopic frame, and sends the optical image to the pick-up unit 6. The pick-up unit 6 converts the input optical image to corresponding image data in the form of an electric signal. The A/D converter 7 converts this image data to digital data. The converted digital image data is input to the image processing unit 13 and also to the memory 8 for storage. One frame of image data stored in the memory 8 is read out and sent to the predicted value calculation unit 27 at the proper timing. The concerning area designating unit 22 designates the desired area on the frame image as a concerning area and data of this concerning area is input previously to the predicted value calculation unit 27.

Figures 20A, 20B:
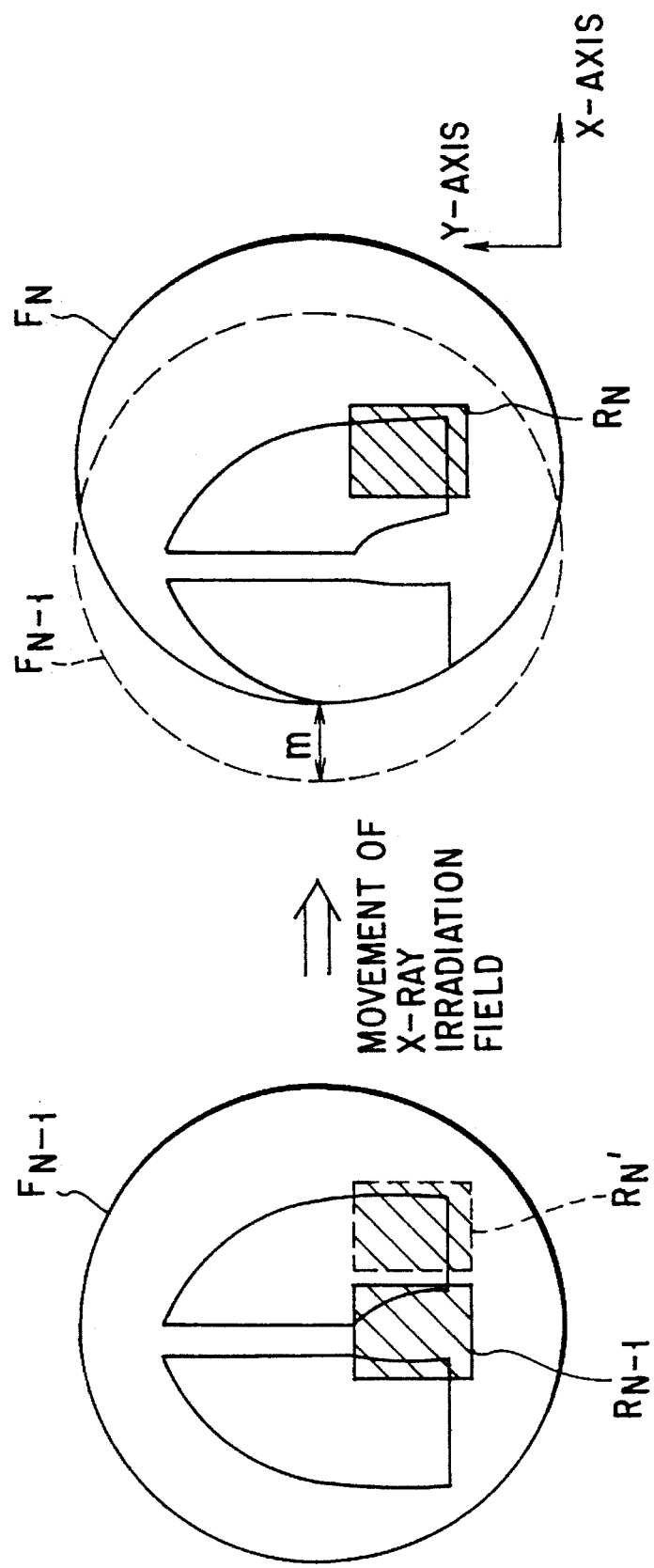
FIGS. 20A and 20B are diagrams for explaining predictive calculation of an image within a concerning area in the next frame according to the sixth embodiment.

Assuming that X-ray fluoroscopy progresses in the order of frames N−2, N−1, N, N+1, and so forth (N: an integer) and the (N−1)-th frame of image data is displayed by, for example, the solid line $F_{N-1}$ in FIG. 20A, then a concerning area on that image data is located in the shaded portion indicated by the solid line $R_{N-1}$. If the operator moves at least one of the supporter 16 and the bed 4 under this situation, the X-ray irradiation field moves accordingly. The first and second movement detectors 9a and 9b output signals according to the moving directions and moving speeds of the bed 4 and the supporter 16 to the predicted value calculation unit 27. This predicted value calculation unit 27 recognizes the movement of the irradiation field, and predicts the moving direction and moving distance (pixel by pixel) of the irradiation field in the next, N-th frame.

If the position of the irradiation field of the N-th frame comes to the position indicated by the solid line $F_N$ shown in FIG. 20B, its moving direction and moving distance can be recognized as the shifting of pixels forming the irradiation field. In other words, in the case of FIG. 20B, the irradiation field $F_{N-1}$ of the (N−1)-th frame is predicted to be the irradiation field $F_N$ of the N-th frame as the field as a whole moves by m pixels in the direction of the X axis (e.g., the direction perpendicular to the body axis of a patient). Based on this pixel shifting (by m pixels) and the previously designated concerning area $R_{N-1}$, the concerning area $R_N$ in the irradiation field $F_N$ in the N-th frame is calculated as the shaded portion $R_N'$ encircled by the broken line in FIG. 20A for the (N−1)-th irradiation field.

This prediction of the concerning area is the same for the irradiation field $F_N$ of the N-th frame and the next (N+1)-th irradiation field $F_{N+1}$ of the next (N+1)-th frame as long as the irradiation field moves. When the image in the irradiation field is not moved, the current frame (e.g., (N−1)-th frame) and the next frame (e.g., N-th frame) overlap each other 100%.

Considering the movement of the irradiation field as the movement of the supporter 16 or the bed 4, a concerning area in the next frame is predicted based on the moving direction and moving speed of the supporter 16 or the bed 4 in the case where the supporter 16 or the bed 4 moves at the maximum allowable speed, and on the concerning area designated in the current frame by the concerning area designating unit 22.

When the concerning area $R_N'$ corresponding to the concerning area $R_N$ in the irradiation field $F_N$ of the N-th frame is predicted from the image data in the irradiation field $F_{N-1}$ of the (N–1)-th frame in the above manner, the image data in this irradiation field $R_N'$ is sent to the adjustment coefficient calculation unit 21. Based on the received image data (pixel value), the calculation unit 21 calculates the brightness and contrast adjustment coefficients for the N-th frame of image data.

While the adjustment coefficients for the N-th frame of image data are being calculated from the (N–1)-th frame of image data, the N-th frame of image data is input to the image processing unit 13 and the memory 8.

The image processing unit 13 performs the brightness and contrast adjustment on the N-th frame of image data using the adjustment coefficients supplied from the adjustment coefficient calculation unit 21. The image data with the adjusted brightness and contrast is sent via the D/A converter 14 to the image display unit 15 to be displayed nearly in real time as an X-ray diagnostic image of the N-th frame.

The brightness and contrast adjustment coefficients for the (N+1)-th frame of image data are calculated from the N-th frame of image data which are temporarily stored in the memory 8 following the N-th frame of image data. Then, the image processing unit 13 adjusts the (N+1)-th frame of image data using the adjustment coefficients based on the predictive self image data. The same processing is repeated thereafter.

When the detection values of the first and second movement detectors 9a and 9b are zero or the irradiation field has not moved, the aforementioned concerning area $R_N'$ and concerning area $R_{N-1}$ overlap each other 100%. Even in this case, the adjustment coefficients are simply calculated based on the image data in that area $R_N'$, and image processing is executed based on the adjustment coefficients.

According to the sixth embodiment, as described above, a concerning area on the next frame of image data is predicted from the position of the moving speed data of the irradiation field and the current concerning area, and predictive image adjustment coefficients for the next frame of image data are obtained using the image data corresponding to the concerning area of the current frame. Using the adjustment coefficients, the brightness and contrast adjustments are performed on the next frame of image data or self image.

Consequently, the X-ray diagnostic image displayed on the image display unit 15 is the self image which has undergone the proper brightness and contrast adjustments, and thus has a high quality with the desired brightness and contrast. This allows the operator to manipulate a catheter more easily.

Figure 3:
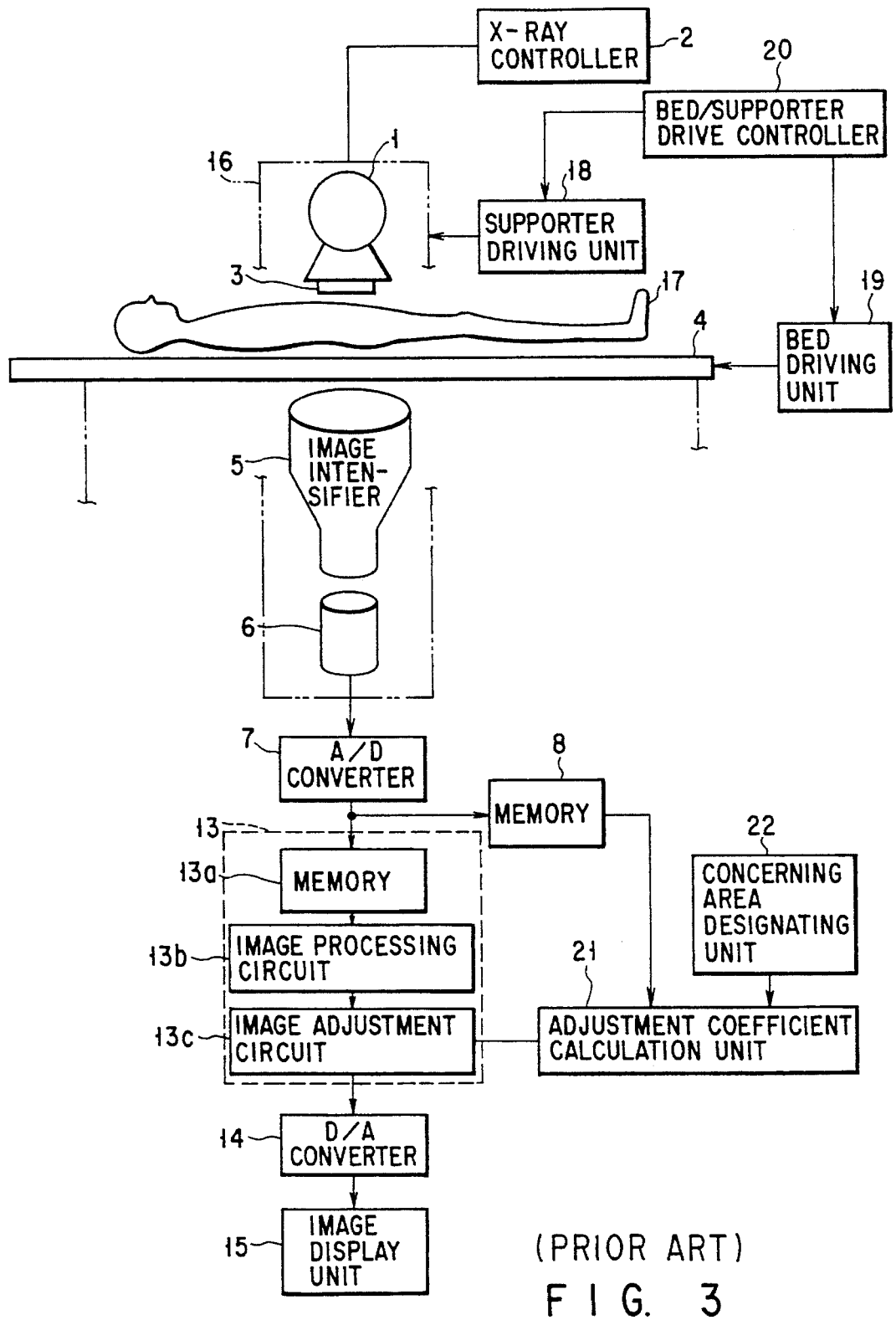
FIG. 3 is a block diagram showing one example of the conventional X-ray diagnosis apparatus.

According to the sixth embodiment, while image adjustment is performed on a self image, a predicting process for the next frame is carried out, so that the image data of the frame to be processed by the image processing unit 13 can be stored in the memory 8. This frame thus precedes the frame of certain image data by one. This design eliminates the need for a frame memory (memory 13a in FIG. 3) in the image processing unit, which is essential in the conventional apparatus, thus causing no frame delay between the X-ray diagnostic image displayed on the image display unit 15 and the currently collected X-ray diagnostic image. This shortens the time from the collection of an image to the display of a processed image.

Even in the case where the operator manipulates a catheter while viewing an X-ray diagnostic image, therefore, the difference between the displayed image and the current image of the actual manipulation and awkward feeling originated from this difference can surely be overcome.

Particularly, when the X-ray irradiation field is moved, the awkward feeling originated from the difference between the displayed image and the current image of the actual manipulation becomes significant. According to the sixth embodiment, however, this problem can surely be overcome and the conventional manipulation trouble originated from the frame delay can be avoided, thus ensuring stable and efficient manipulation. This reduces the burden on the operation significantly.

Although the adjustment coefficients calculated by the adjustment coefficient calculation unit 21 are sent to the image adjustment circuit 13c to adjust the brightness and contrast of an X-ray diagnostic image, the adjustment coefficients may be output to the X-ray controller 2 to adjust the output of the X-ray tube 1, thereby adjusting the brightness and contrast of the X-ray diagnostic image.

Although the foregoing description of the sixth embodiment has been given with reference to the case where the automatic adjustment of the brightness and contrast is performed as image processing, other adjustment processes such as spatial filtering and time filtering may also be employed in the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray diagnosis apparatus comprising:

a bed on which an object is placed;

supporting means on which X-ray irradiation means for irradiating a predetermined amount of X-rays to said object on said bed and converting means for converting X-rays passed through said object into an object image signal are mounted;

first moving means for moving said bed;

second moving means for moving said supporting means; and drive control means for controlling movement of at least said converting means in such a manner that said object appears to be stopped as viewed from said converting means while said bed and said supporting means are moved relative to each other by said first moving means and said second moving means and X-rays are irradiated from said X-ray irradiation means.

2. The X-ray diagnosis apparatus according to claim 1, wherein said drive control means includes means for controlling said second moving means.

3. The X-ray diagnosis apparatus according to claim 1, further comprising:

first detecting means for detecting a moving direction and moving speed of said bed; and second detecting means for detecting a moving direction and moving speed of said supporting means; and wherein said converting means includes X-ray incident surface for receiving X-rays passed through said object, and said drive control means includes means for converting an amount of a change of said bed with respect to said supporting means during X-ray irradiation to an amount of a change on the X-ray incident surface of said converting means based on said moving directions and moving speeds detected by said first detecting means and said second detecting means, and controlling said second moving means in accordance with said change amount.

4. The X-ray diagnosis apparatus according to claim 1, further comprising third moving means for moving at least said converting means; and wherein said drive control means includes means for controlling said third moving means.

5. The X-ray diagnosis apparatus according to claim 4, further comprising:

first detecting means for detecting a moving direction and moving speed of said bed; and second detecting means for detecting a moving direction and moving speed of said supporting means; and wherein said converting means includes X-ray incident surface for receiving X-rays passed through said object, and said drive control means includes means for converting an amount of a change of said bed with respect to said supporting means during X-ray irradiation to an amount of a change on the X-ray incident surface of said converting means based on said moving directions and moving speeds detected by said first detecting means and said second detecting means, and controlling said third moving means in accordance with said change amount.

6. The X-ray diagnosis apparatus according to claim 5, wherein said drive control means includes means for multiplying an amount of a change of said bed to said supporting means during X-ray irradiation by a geometric magnification, obtained from a relative ratio of a distance from said X-ray irradiation means to said converting means to a distance from said object to said converting means, thereby obtaining an amount of a change the said X-ray incident surface of said converting means.

7. The X-ray diagnosis apparatus according to claim 1, wherein said converting means includes:

means for converting X-rays passed through said object to an optical image; and pick-up means for converting said optical image of said object into an image signal, and further comprising moving means for moving said pick-up means, wherein said drive control means includes means for controlling said fourth moving means.

8. The X-ray diagnosis apparatus according to claim 7, further comprising:

first detecting means for detecting a moving direction and moving speed of said bed; and second detecting means for detecting a moving direction and moving speed of said supporting means; and wherein said converting means includes X-ray incident surface for receiving X-rays passed through said object, and said drive control means includes means for converting an amount of a change of said bed with respect to said supporting means during X-ray irradiation to an amount of a change the X-ray incident surface of said converting means based on said moving directions and moving speeds detected by said first detecting means and said second detecting means, and controlling said fourth moving means in accordance with said change amount.

9. The X-ray diagnosis apparatus according to claim 8, wherein said drive control means includes means for multiplying an amount of a change of said bed to said supporting means during X-ray irradiation by a geometric magnification, obtained from a relative ratio of a distance from said X-ray irradiation means to said converting means to a distance from said object to said converting means, thereby obtaining an amount of a change on the X-ray incident surface of said converting means.

10. An X-ray diagnosis apparatus comprising:

a bed on which an object is placed;

supporting means on which X-ray irradiation means for irradiating a predetermined amount of X-rays to said object on said bed, converting means for converting X-rays passed through said object into an optical image, and pick-up means for converting said optical image into an image signal are mounted;

first moving means for moving said bed;

second moving means for moving said supporting means; and drive control means for controlling relative movement of said pick-up means to said converting means in such a manner that an image on a pick-up surface of said converting means is stopped while said bed and said supporting means are moved relative to each other by said first moving means and said second moving means and X-rays are irradiated from said X-ray irradiation means.

11. The X-ray diagnosis apparatus according to claim 10, further comprising:

first detecting means for detecting a moving direction and moving speed of said bed; and second detecting means for detecting a moving direction and moving speed of said supporting means; and wherein said converting means includes X-ray incident surface for receiving X-rays passed through said object, and said drive control means includes means for converting an amount of a change of said bed with respect to said supporting means during X-ray irradiation to an amount of a change on the X-ray incident surface of said converting means based on said moving directions and moving speeds detected by said first detecting means and said second detecting means, and controlling said second moving means in accordance with said change amount.

12. The X-ray diagnosis apparatus according to claim 11, wherein said drive control means includes means for multiplying an amount of a change of said bed to said supporting means during X-ray irradiation by a geometric magnification, obtained from a relative ratio of a distance from said X-ray irradiation means to said converting means to a distance from said object to said converting means, thereby obtaining an amount of a change on the X-ray incident surface of said converting means.

13. An X-ray diagnosis apparatus comprising:

a bed on which an object is placed;

supporting means on which X-ray irradiation means for irradiating a predetermined amount of X-rays to said object on said bed and converting means for converting X-rays passed through said object into an object image signal are mounted;

moving means for moving said bed and said supporting means relative to each other; and optical path changing means for changing an optical path from said converting means to said supporting means in such a manner that an image on a pick-up surface of said converting means is stopped while said bed and said supporting means are moved relative to each other by said moving means and X-rays are irradiated from said X-ray irradiation means.

14. The X-ray diagnosis apparatus according to claim 13, further comprising:

first detecting means for detecting a moving direction and moving speed of said bed; and second detecting means for detecting a moving direction and moving speed of said supporting means; and wherein said optical path changing means includes:

a plate mirror inclined to an optical axis of output light from said converting means;

mirror driving means for driving said mirror to make parallel movement in a same direction as a direction of relative movement of said bed to said supporting means; and control means for converting an amount of a change of said bed with respect to said supporting means during X-ray irradiation to an amount of a change on a light output surface of said converting means based on said moving directions and moving speeds detected by said first detecting means and said second detecting means, and controlling said mirror driving means in accordance with said change amount to make parallel movement of said mirror.

15. The X-ray diagnosis apparatus according to claim 14, wherein said drive control means includes means for multiplying an amount of a change of said bed to said supporting means during X-ray irradiation by a geometric magnification, obtained from a relative ratio of a distance from said X-ray irradiation means to said converting means to a distance from said object to said converting means and an optical magnification specific to said converting means, thereby obtaining an amount of a change on said light output surface of said converting means.

16. The X-ray diagnosis apparatus according to claim 13, further comprising:

first detecting means for detecting a moving direction and moving speed of said bed; and second detecting means for detecting a moving direction and moving speed of said supporting means; and wherein said optical path changing means includes:

a light transmittive, parallel planar plate supported rotatably with respect to a rotational axis perpendicular to an optical axis of output light from said converting means;

parallel planar plate driving means for rotating said parallel planar plate in a same direction as a direction of relative movement of said bed to said supporting means; and control means for converting an amount of a change of said bed with respect to said supporting means during X-ray irradiation to an amount of a change on a light output surface of said converting means based on said moving directions and moving speeds detected by said first detecting means and said second detecting means, calculating a rotational angle of said parallel planar plate in accordance with said change amount, and controlling said parallel planar plate driving means to rotate said parallel planar plate by said rotational angle from a position perpendicular to said optical axis of said output light from said converting means.

17. The X-ray diagnosis apparatus according to claim 13, further comprising:

first detecting means for detecting a moving direction and moving speed of said bed; and second detecting means for detecting a moving direction and moving speed of said supporting means; and wherein said optical path changing means includes:

a plate mirror inclined to an optical axis of output light from said converting means;

mirror driving means for rotating said mirror in accordance with a direction of relative movement of said bed to said supporting means; and control means for converting an amount of a change of said bed with respect to said supporting means during X-ray irradiation to an amount of a change on a light output surface of said converting means based on said moving directions and moving speeds detected by said first detecting means and said second detecting means, calculating a rotational angle of said mirror in accordance with said change amount, and controlling said mirror driving means to move said mirror by said rotational angle from a position perpendicular to said optical axis of said output light from said converting means.

18. The X-ray diagnosis apparatus according to claim 13, further comprising:

first detecting means for detecting a moving direction and moving speed of said bed; and second detecting means for detecting a moving direction and moving speed of said supporting means; and wherein said optical path changing means includes:

a prism located in a path of output light from said converting means;

prism driving means for rotating said prism in a same direction as a direction of relative movement of said bed to said supporting means; and control means for converting an amount of a change of said bed with respect to said supporting means during X-ray irradiation to an amount of a change on a light output surface of said converting means based on said moving directions and moving speeds detected by said first detecting means and said second detecting means, calculating a rotational angle of said prism in accordance with said change amount, and controlling said prism driving means to rotate said prism by said rotational angle from a position perpendicular to said optical axis of said output light from said converting means.

19. An X-ray diagnosis apparatus comprising:

a bed on which an object is placed;

supporting means on which X-ray irradiation means for irradiating a predetermined amount of X-rays to said object on said bed and converting means for converting X-rays passed through said object into an object image signal are mounted;

first moving means for moving said bed;

second moving means for moving said supporting means;

X-ray control means for controlling said X-ray irradiation means in such a way that at least two X-ray irradiations are executed in one period for obtaining a single image of said object;

correction amount calculation means for correcting a moving direction and a moving mount for at least a single second image obtained through an X-ray irradiation following a first X-ray irradiation in said one period by relative movement between said bed and said supporting means in such a manner that said second image overlaps a first image obtained by said first X-ray irradiation in said one period;

image correction means for correcting said second image in such a manner that said second image overlaps said first image based on said moving direction and moving amount for said second image, obtained by said correction calculation means;

image adding means for adding said first image and said second image after correction; and image display means for displaying an image resulting from said addition.

20. The X-ray diagnosis apparatus according to claim 19, wherein said X-ray irradiation means includes means for irradiating an X-ray pulse to said object with an X-ray pulse width for allowing a sum of irradiation times to provide a desired dose of X-rays and with an irradiation interval of said X-ray pulse equal to or longer than a time interval associated with transfer of accumulated charges on a light receiving surface of said converting means.

21. The X-ray diagnosis apparatus according to claim 19, wherein said X-ray irradiation means includes an X-ray limiter for preventing X-ray irradiation to a non-common area other than a portion where at least two images of said object, obtained by at least two irradiations, overlap.

22. An X-ray diagnosis apparatus comprising:

X-ray irradiation means for irradiating X-rays toward a diagnosing portion of an object;

converting means for converting X-rays passed through said object to image data;

storage means for temporarily storing said image data, converted by said converting means, frame by frame;

detecting means for detecting a moving direction and a moving speed of an irradiation field of said X-rays with respect to said object;

designating means for designating a concerning area in said image data;

area predicting means for predicting an area to be a concerning area in a next frame, based on detection values of said detecting means and said concerning area designated by said designating means;

adjustment coefficient calculation means for calculating an image adjustment coefficient based on said image data in said storage means corresponding to said concerning area predicted by said area predicting means;

image adjusting means for performing a desired image adjustment according to said image adjustment coefficient, calculated by said adjustment coefficient calculation means, on said image data converted by said converting means; and display means for displaying said image data having undergone said image adjustment.

23. The X-ray diagnosis apparatus according to claim 22, wherein said image adjusting means includes means for adjusting at least one of brightness and contrast of an X-ray fluoroscopic image.

24. The X-ray diagnosis apparatus according to claim 22, wherein said image adjusting means includes means for adjusting an output of said X-ray irradiation means based on said image adjustment coefficient.

* * * * *